US011065336B2

(12) United States Patent
Crowther et al.

(10) Patent No.: US 11,065,336 B2
(45) Date of Patent: Jul. 20, 2021

(54) CONJUGATES FOR TARGETING AND CLEARING AGGREGATES

(71) Applicant: MedImmune Limited, Cambridge (GB)

(72) Inventors: Damian C. Crowther, Cambridge (GB); Maria Herva, Cambridge (GB); Roland Bürli, Cambridge (GB); Lutz Jermutus, Cambridge (GB)

(73) Assignee: MEDIMMUNE LIMITED, Cambridge (GB)

( * ) Notice: Subject to any disclaimer, the term of this patent is extended or adjusted under 35 U.S.C. 154(b) by 0 days.

(21) Appl. No.: 16/397,377

(22) Filed: Apr. 29, 2019

(65) Prior Publication Data

US 2019/0328889 A1 Oct. 31, 2019

Related U.S. Application Data

(60) Provisional application No. 62/664,345, filed on Apr. 30, 2018.

(51) Int. Cl.

*A61K 47/54* (2017.01)
*A61K 47/62* (2017.01)
*A61P 25/28* (2006.01)
*A61K 38/10* (2006.01)

(52) U.S. Cl.

CPC ............ *A61K 47/545* (2017.08); *A61K 38/10* (2013.01); *A61K 47/62* (2017.08); *A61P 25/28* (2018.01)

(58) Field of Classification Search

None

See application file for complete search history.

(56) References Cited

FOREIGN PATENT DOCUMENTS

WO WO-2009/090268 A1 7/2009
WO WO-2014/178878 A1 11/2014

OTHER PUBLICATIONS

Schulke ("The homodimer of prostate-specific membrane antigen is a functional target for cancer therapy," PNAS, 2003, vol. 100, pp. 12590-12595) (Year: 2003).*

Al-Shawi, et al., "Pharmacological removal of serum amyloid P component from intracerebral plaques and cerebrovascular Aβ amyloid deposits in vivo," Open Biology, vol. 6: 1-8 (2016).

Biancalana, et al., "Molecular Mechanism of Thioflavin-T Binding to Amyloid Fibrils," Biochim Biophys Acta, vol. 1804(7): 1405-1412 (2010).

Bonetto, et al., "Identification of cyclic peptides able to mimic the functional epitope of IgG1-Fc for Human FcγRI," The FASEB Journal, vol. 23: 575-585 (2009).

Frost, et al., "Prion-like Mechanisms in Neurodegenerative Diseases," Nature Reviews Neuroscience, vol. 11(3): 155-159 (2010).

McEnaney, et al., "Chemically Synthesized Molecules with the Targeting and Effector Functions of Antibodies," Journal of the American Chemical Society, vol. 136: 18034-18043 (2014).

Richards, et al., "Therapeutic Clearance of Amyloid by Antibodies to Serum Amyloid P Component," The New England Journal of Medicine: 1-9 (2015).

Sigma-Aldrich, Safety Data Sheet, Thioflavin T, 7 pages (2019).

Bard F et al: Peripherally administered antibodies against amyloid beta—peptide enter the central nervous system and reduce pathology in a mouse model of Alzheimer disease, Nature Medicine, Nature Pub. Co, New York, vol. 6, No. 8, Aug. 1, 2000 (Aug. 1, 2000), pp. 916-919.

* cited by examiner

*Primary Examiner* — Christina Bradley

(74) *Attorney, Agent, or Firm* — White & Case LLP

(57) ABSTRACT

In some embodiments, the disclosure provides for a conjugate comprising: a) a peptide that competes with an Fc fragment of an IgG for binding to an Fc receptor; and b) a targeting moiety that targets molecular aggregates. In some embodiments, the disclosure provides for methods of using the conjugates for treating a disease or disorder associated with aggregate formation.

12 Claims, 9 Drawing Sheets
(8 of 9 Drawing Sheet(s) Filed in Color)
Specification includes a Sequence Listing.

SEQUENCE LISTING

<160> NUMBER OF SEQ ID NOS: 22

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (7)..(7)
<223> OTHER INFORMATION: Any hydrophobic amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (14)..(14)
<223> OTHER INFORMATION: Any acidic amino acid
<220> FEATURE:
<221> NAME/KEY: MOD_RES
<222> LOCATION: (15)..(15)
<223> OTHER INFORMATION: Any amino acid

<400> SEQUENCE: 1

Thr Xaa Xaa Cys Xaa Xaa Xaa Pro Xaa Leu Leu Gly Cys Xaa Xaa Glu
1 5 10 15

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2

Ala Gln Val Asn Ser Cys Leu Leu Leu Pro Asn Leu Leu Gly Cys
1 5 10 15

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 3

Ala Gln Val Asn Ser Cys Leu Leu Leu Pro Asn Leu Leu Gly Cys Gly
1 5 10 15

Asp Asp Lys

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 4

Thr Asp Thr Cys Leu Met Leu Pro Leu Leu Leu Gly Cys Asp Glu Glu
1 5 10 15

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 5

Asp Pro Ile Cys Trp Tyr Phe Pro Arg Leu Leu Gly Cys Thr Thr Leu
1 5 10 15

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 6

```
Trp Tyr Pro Cys Tyr Ile Tyr Pro Arg Leu Leu Gly Cys Asp Gly Asp
1               5                   10                  15
```

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 7

```
Gly Asn Ile Cys Met Leu Ile Pro Gly Leu Leu Gly Cys Ser Tyr Glu
1               5                   10                  15
```

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 8

```
Val Asn Ser Cys Leu Leu Leu Pro Asn Leu Leu Gly Cys Gly Asp Asp
1               5                   10                  15
```

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 9

```
Thr Pro Val Cys Ile Leu Leu Pro Ser Leu Leu Gly Cys Asp Thr Gln
1               5                   10                  15
```

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 10

```
Thr Val Leu Cys Ser Leu Trp Pro Glu Leu Leu Gly Cys Pro Pro Glu
1               5                   10                  15
```

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 11

Thr Phe Ser Cys Leu Met Trp Pro Trp Leu Leu Gly Cys Glu Ser Leu
1 5 10 15

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 12

Phe Gly Thr Cys Tyr Thr Trp Pro Trp Leu Leu Gly Cys Glu Gly Phe
1 5 10 15

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 13

Ser Leu Phe Cys Arg Leu Leu Leu Thr Pro Val Gly Cys Val Ser Gln
1 5 10 15

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 14

His Leu Leu Val Leu Pro Arg Gly Leu Leu Gly Cys Thr Thr Leu Ala
1 5 10 15

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 15

Thr Ser Leu Cys Ser Met Phe Pro Asp Leu Leu Gly Cys Phe Asn Leu
1 5 10 15

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 16

Ser His Pro Cys Gly Arg Leu Pro Met Leu Leu Gly Cys Ala Glu Ser
1 5 10 15

```
<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Thr Ser Thr Cys Ser Met Val Pro Gly Pro Leu Gly Ala Val Ser Thr
1               5                   10                  15

Trp


<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Asp Pro Cys Thr Arg Trp Ala Met Leu Leu Gly Cys Asp Gly Glu
1               5                   10                  15


<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ile Met Thr Cys Ser Val Tyr Pro Phe Leu Leu Gly Cys Val Asp Lys
1               5                   10                  15


<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ile His Ser Cys Ala His Val Met Arg Leu Leu Gly Cys Trp Ser Arg
1               5                   10                  15


<210> SEQ ID NO 21
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ala Gln Val Asn Ser Cys Leu Leu Leu Pro Asn Leu Leu Gly Cys Ser
1               5                   10                  15

Tyr Glu Lys Lys Lys Lys Lys Glu Tyr Ser Cys Gly Leu Leu Asn Pro
            20                  25                  30

Leu Leu Leu Cys Asn Val Gln Ala
        35                  40
```

-continued

```
<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys Lys Lys Lys Lys
1               5
```

CONJUGATES FOR TARGETING AND CLEARING AGGREGATES

CROSS-REFERENCE TO RELATED APPLICATION

This application claims the benefit of priority from U.S. Provisional Application No. 62/664,345, filed on Apr. 30, 2018. The foregoing application is incorporated herein by reference in its entirety.

SEQUENCE LISTING

The instant application contains a Sequence Listing which has been submitted electronically in ASCII format and is hereby incorporated by reference in its entirety. Said ASCII copy, created on Apr. 26, 2019, is named 1848081-0002-107_101_SL.txt and is 7,036 bytes in size.

BACKGROUND OF THE INVENTION

Numerous diseases and disorders are caused by or associated with aggregates of proteins, polysaccharides, lipids and/or nucleotides. In many cases, these aggregates are considered to be toxic. These diseases affect various cells, tissues and organs throughout the body.

Amyloidosis is a category of diseases associated with accumulation of abnormal protein conformers, known as amyloid fibrils, in tissues. Clinical features depend on the type of amyloidosis, and may include diarrhea, weight loss, fatigue, glossomegaly, haemorrhage, somatic sensory deficits, postural hypotension, peripheral edema and splenomegaly. Treatment of amyloidosis typically addresses symptoms only, and may not be effective. Examples of amyloidosis include AL amyloidosis, AA amyloidosis, transthyretin amyloidosis, leptomeningeal amyloidosis, type II diabetes, and certain neurodegenerative diseases such as Alzheimer's Disease and Creutzfeldt-Jakob Disease.

Glycogen storage diseases are a series of diseases typically associated with enzyme deficiencies resulting in aberrant glycogen synthesis or glycolysis. These diseases may be genetic or acquired and symptoms vary depending on the type of disease. Examples of glycogen storage diseases include GSDI-XV. Treatment is typically a diet of limited carbohydrates, but may include treatment with allopurinol and/or human granulocyte colony stimulating factor.

Lipid aggregate diseases include atherosclerosis, heart disease, and neurodegenerative diseases such as Niemann-Pick Type C disease. Diseases in which abnormally aggregating RNA molecules have been implicated include Dentatorubral pallidoluysian atrophy (DRPLA), Huntington chorea (HD), Oculopharyngeal muscular dystrophy (OPMD), Spinobulbar muscular atrophy (SBMA), and Spinocerebellar ataxia types 1, 2, 3, 6, 7, and 17 (SCA1, SCA2, SCA3, SCA6, SCAT, SCA1 7), Fragile XA, Fragile XE, Friedrich's ataxia, Myotonic Dystrophy type 1 (DM1), Myotonic Dystrophy type 2 (DM2), Spinocerebellar ataxia types 8, 10, and 12 (SCAB, SCA 10, SCA 12), amyotrophic lateral sclerosis and fronotemporal dementia (FTD). These diseases lack an effective treatment capable of clearing the aggregates.

Degenerative diseases of the nervous system impose a significant worldwide medical and public health burden. The prevalence and incidence of these diseases rise dramatically with age and the number of cases is expected to increase with extended life expectancy in many countries (Checkoway H et al. IARC Sci Publ. 2011; (163):407-19). Alzheimer's Disease International (ADI) estimated in 2015 that there were 46.8 million people with Alzheimer's Disease worldwide, and that this number will grow to 131.5 million people by 2050 (Prince M. et al. ADI Report. 2016 Sep. 20; 1-131). An estimated 5.7 million Americans of all ages have Alzheimer's disease in 2018, of which 5.5 million people are age 65 and older (Alzheimer's Association. 2018 Alzheimer's Disease Facts and Figures. Alzheimers Dement 2018; 14(3):367-429). By 2050, the number of people age 65 and older with Alzheimer's disease in the U.S. may nearly triple, from 5.1 million to a projected 14 million, in the absence of medical intervention to prevent or cure the disease. Id.

Neurodegenerative diseases are commonly associated with the accumulation of intracellular or extracellular protein aggregates, such as α-synuclein in Parkinson's disease, β-amyloid and tau in Alzheimer's disease, huntingtin in Huntington's disease and prion protein (PrP) in transmissible prion encephalopathies (Brundin P et al. Nat Rev Mol Cell Biol. 2010 April; 11(4): 301-307). Other systemic degenerative diseases, some of which occur outside the nervous system, are also attributed to α-synuclein, β-amyloid, huntingtin, prion protein, and amylin. These include diseases such as type II diabetes, characterized by amylin deposition, and amyloidosis, a rare disease in which amyloid protein builds up in various organs and tissues such as the heart, kidney, liver, spleen, nervous system, or digestive tract.

A new understanding is emerging about protein aggregate disorders such as Alzheimer's Disease, Parkinson's Disease, Huntington's Disease, amyotrophic lateral sclerosis (ALS), transmissible spongiform encephalopathies (TSEs), motor neuron diseases, tauopathies, type II diabetes, amyloidosis etc that involve protein misfolding. Evidence suggests that protein-misfolding and subsequent propagation of these rogue proteins is a generic phenomenon shared with diseases caused by tau, α-synucleins and β-amyloid proteins (Panegyres P K and Armari E. Am J Neurodegener Dis. 2013; 2(3): 176-186). The deposition of aggregated protein is a central feature of these otherwise unrelated pathological conditions.

Protein aggregation of α-synuclein, β-amyloid, huntingtin, prion protein typically begins when several identical monomeric proteins self-associate to change conformation from native structure to aggregated structures. It is believed that in the majority of aggregation diseases, a conformational transition from native structure to β-sheet-rich oligomeric structures is critical even in the fibrillation process (Morales B et al. CNS Neurol Disord Drug Targets. 2009 November; 8(5): 363-371). Thus, numerous therapies attempt to block propagation of protein misfolding throughout the brain and body (Frost B and Diamond M I. Nat Rev Neurosci. 2010 March; 11(3): 155-159). Some of these strategies include (1) inhibition of the production of amyloid polypeptides, (2) inhibition of the formation of amyloid fibrils, and (3) destabilization of amyloid structures using compounds, antibodies, vaccines, small molecules, antioxidants, destabilizing peptides, or natural extracts.

There is currently no cure for aggregate diseases such as Alzheimer's Disease, and the prognosis in Alzheimer's Disease is poor. As of 2018, the majority of treatments are limited to symptomatic management which consists primarily of acetylcholinesterase inhibitors. There are only five approved medications in the US for treating Alzheimer's Disease (Aricept®, Exelon®, Razadyne®, Namenda®, and Donepezil®). These medications temporarily slow the worsening of symptoms and improve quality of life for those with Alzheimer's and their caregivers. However, they do not cure Alzheimer's or stop it from progressing.

In view of the lack of effective therapeutic options for aggregate-associated diseases or disorders, there is a need for innovative therapeutics for treating these diseases or disorders.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

SUMMARY OF THE INVENTION

Figure 1:
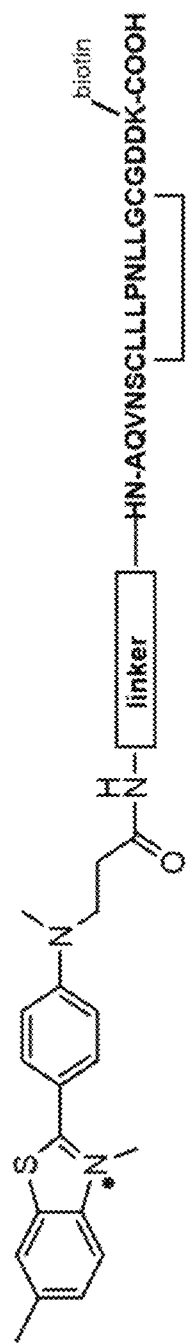
FIG. 1 shows a schematic of the synthesis of BDB, a conjugate comprising a specific carboxylic acid derivative of thioflavin T (Compound 1) and a specific targeting moiety (cp33 peptide derivative; SEQ ID NO:3). As shown, Compound 1 is added as the terminal residue of the biotinylated synthetic cyclic peptide, which is a derivative of the cp33 peptide (Bonetto S et al. FASEB J. 2009; 23(2):575-85), via a linker. In some embodiments, linkers may comprise 13-alanine, 9-amino-4,7-dioxanonanoic acid and/or 6-amino-4-oxaohexanoic acid.

In some embodiments, the disclosure provides for a conjugate comprising: a) a peptide that competes with an Fc fragment of an IgG for binding to an Fc receptor; and b) a targeting moiety that targets molecular aggregates. In some embodiments, the peptide activates Fc effector function. In some embodiments, the Fc receptor is selected from the group consisting of: FcγRI, FcγRII, and FcγRIII. In some embodiments, the Fc receptor is a human receptor. In some embodiments, the Fc receptor is any one of a FcγRI, FcRn, TREM2, CD33, TMEM119, CD11b, CD45, Iba1, CX3CR1, CD68, P2X family or P2Y family receptor. In some embodiments, the Fc receptor is TREM2. In some embodiments, the Fc receptor is FcRn. In some embodiments, the Fc receptor is human FcγRI (hFcγRI). In some embodiments, the Fc effector function is phagocytosis. In some embodiments, the peptide competes with the Fc portion of an IgG3 or IgG1 antibody. In some embodiments, the peptide competes with the Fc portion of IgG1. In some embodiments, the peptide comprises a tripeptide motif of LLG. In some embodiments, the peptide comprises a dimer of motif ζP and wherein ζ represents a hydrophobic residue. In some embodiments, the peptide comprises threonine at an N-terminus of the peptide. In some embodiments, the peptide comprises glutamic acid at a C-terminus of the peptide. In some embodiments, the peptide comprises an amino acid sequence of TX2CXXζPXLLGCφXE (SEQ ID NO: 1); wherein X is any amino acid, ζ is a hydrophobic residue and φ is an acidic amino acid. In some embodiments, the peptide binds specifically to hFcγRI and does not exhibit cross-reactivity with hFcγRII or hFcγRIII. In some embodiments, the peptide comprises the amino acid sequence of AQVNSCLLLPNLLGC (SEQ ID NO: 2). In some embodiments, the peptide comprises the amino acid sequence of AQVNSCLLLPNLLGCGDDK (SEQ ID NO: 3). In some embodiments, one or more amino acid residues in the peptide are methylated. In some embodiments, the asparagine residue at the amino acid position corresponding to position 11 of SEQ ID NO: 2 or 3 is methylated. In some embodiments, the leucine residue at the amino acid position corresponding to position 13 of SEQ ID NO: 2 or 3 is methylated.

In some embodiments, the disclosure provides for a conjugate multimer comprising two or more of any of the conjugates disclosed herein, linked to each other to generate a dimeric or oligomeric peptide. In some embodiments, the peptide binds to two hFcγRIs and activates Fc effector function. In some embodiments, the conjugate comprises two Fc mimetic peptides linked by a KKKKK linker (SEQ ID NO: 22). In some embodiments, the conjugate is capable of recruiting an immune cell to the molecular aggregates. In some embodiments, the immune cell is a monocyte-derived cell. In some embodiments, the immune cell is a macrophage. In some embodiments, the immune cell is a monocyte. In some embodiments, the immune cell is a microglial cell. In some embodiments, the conjugate binds to the immune cell and facilitates activation of the immune cell. In some embodiments, the conjugate facilitates phagocytosis of at least a portion of the molecular aggregates. In some embodiments, the targeting moiety targets protein aggregates. In some embodiments, the protein aggregates comprise aggregates of any one of the following proteins: alpha-synuclein, tau, amyloid beta, TDP-43, SOD1, FUS, TDP-43, prion protein, immunoglobulin light chain, transthyretin, fibrinogen, collagen, islet amyloid polypeptide, lysozyme, calcitonin, serum amyloid A protein, LECT2, amylin, gelsolin, fibrinogen A, prolactin, keratoepithelin, and $\beta_2$-microglobin. In some embodiments, the targeting moiety targets lipid aggregates. In some embodiments, the lipid aggregates are cholesterol aggregates. In some embodiments, the targeting moiety targets polysaccharide aggregates. In some embodiments, the targeting moiety targets glycogen aggregates. In some embodiments, the targeting moiety is a small molecule. In some embodiments, the targeting moiety is a peptide. In some embodiments, the targeting moiety is a nucleic acid. In some embodiments, the targeting moiety is a dye. In some embodiments, the dye binds to amyloid. In some embodiments, the dye is selected from the group consisting of: a thioflavin, pentamer formyl thiophene acetic acid (pFTAA), heptamer formyl thiophene acetic acid (hFTAA), Congo Red, crystal violet, 1-amino-8-naphtalene sulphonate (ANS), 4-(dicyanovinyl)-julolidine (DCVJ), aminobenzanthrone, Methoxy XO4, thiazin red, Pittsburgh B, and amyloid-binding derivatives thereof. In some embodiments, the thioflavin is thioflavin T, or an amyloid-binding derivative thereof. In some embodiments, the amyloid comprises any one or more of the following proteins: alpha-synuclein, tau, amyloid beta, TDP-43, SOD1, FUS, C79ORF, TDP-43, prion protein, immunoglobulin light chain, transthyretin, fibrinogen, collagen, islet amyloid polypeptide, lysozyme, calcitonin, serum amyloid A protein, LECT2, amylin, gelsolin, fibrinogen A, prolactin, keratoepithelin, and $\beta_2$-microglobin. In some embodiments, the amyloid comprises lysozyme. In some embodiments, the dye binds to cholesterol. In some embodiments, the dye is filipin, or a cholesterol-binding derivative thereof. In some embodiments, the dye binds to collagen. In some embodiments, the dye is sirius red, Col-F, Oregon Green 488, or Picrosirius red, Light Green SF yellowish, Fast Green FCF, methyl blue, water blue, aniline blue, and collagen-binding derivatives thereof. In some embodiments, the dye binds polysaccharide aggregates. In some embodiments, the dye binds glycogen aggregates. In some embodiments, the dye is selected from the group consisting of periodic acid, alcian blue, and Dimethyl methylene blue. In some embodiments, the dye binds nucleotide aggregates. In some embodiments, the dye binds to RNA aggregates. In some embodiments, the dye binds DNA aggregates. In some embodiments, the targeting moiety has been modified to facilitate conjugation to the peptide. In some embodiments, the targeting moiety has been modified such that it includes a carboxyl group. In some embodiments, the carboxyl group of the targeting moiety is bonded to the amino terminus of the peptide. In some embodiments, the targeting moiety has been modified such that it includes an amino group. In some embodiments, the amino group of the targeting moiety is bonded to the carboxy terminus of the peptide.

In some embodiments, the targeting moiety is conjugated to the peptide by means of a linker. In some embodiments, the linker is a non-cleavable linker, hydrazone linker, thioether linker, disulfide linker, peptide linker or β-glucuronide linker. In some embodiments, the linker is a rigid linker. In some embodiments, the linker comprises the structure of Compound II.

(Compound II)

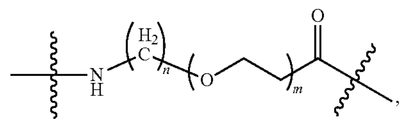

wherein n is 1-30, and m is 0, 1, 2, 3, 4, or 5. In some embodiments, n is 1-25, 1-20, 1-15, 1-10, 1-8, 1-6, 1-4, 1-2 or 1. In some embodiments, n is 2. In some embodiments, m is 0. In some embodiments, the linker is a β-alanine linker, a short polyethylene glycol (PEG) linker, or a long PEG linker. In some embodiments, the linker is a β-alanine linker.

In some embodiments, the conjugate is further conjugated to an additional heterologous moiety. In some embodiments, the heterologous moiety is biotin. In some embodiments, the conjugate comprises the amino acid sequence of AQVNSCLLLPNLLGCGDDK (SEQ ID NO: 3) fused to thioflavin T, or a derivative thereof. In some embodiments, the conjugate comprises the amino acid sequence of AQVNSCLLLPNLLGCGDDK (SEQ ID NO: 3) fused to Compound I:

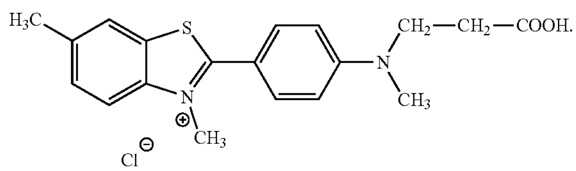

In some embodiments, the conjugate comprises the structure of Compound III:

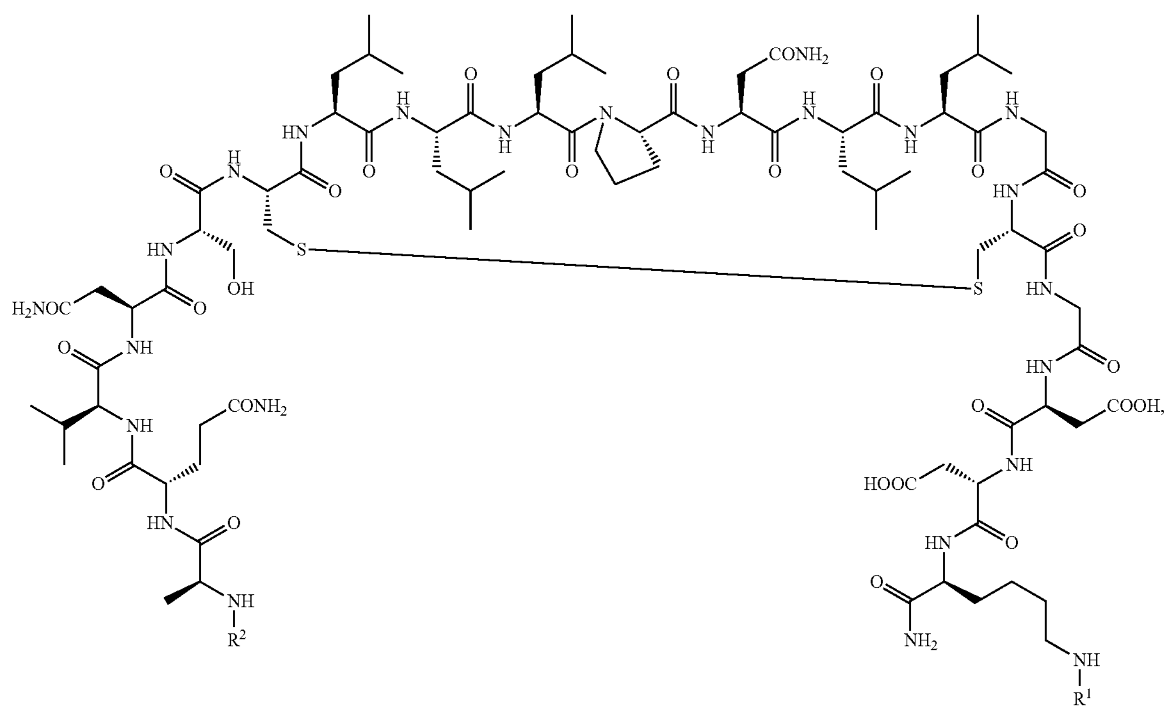

wherein $R^1$ is biotin or hydrogen;
wherein $R^2$ comprises:

a)

Compound IV

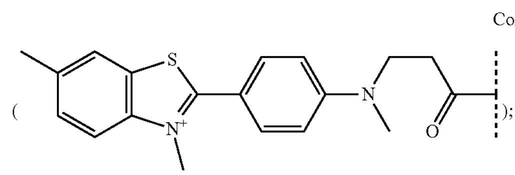

b)

Compound V

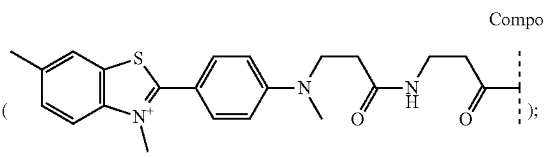

c)

Compound VI

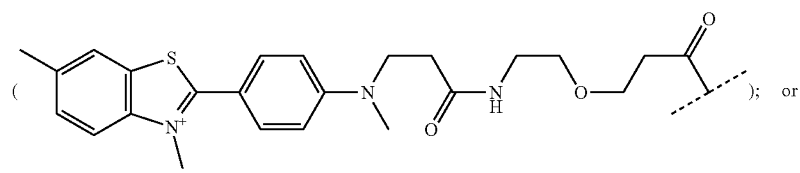

d)

Compound VII

In some embodiments, $R^1$ is biotin. In some embodiments, $R^1$ is hydrogen. In some embodiments, $R^2$ comprises Compound V In some embodiments, the disclosure provides for a method of treating an amyloidosis by administering any one or more of the conjugates disclosed herein. In some embodiments, the amyloidosis is selected from the group consisting of: AL amyloidosis, AA amyloidosis, Alzheimer Disease, LECT2 amyloidosis, leptomeningeal amyloidosis, senile systemic amyloidosis, familial amyloid polyneuropathy, haemodialysis-associated amyloidosis, type 2 diabetes, Creutzfeldt-Jakob disease, Gerstmann-Straussler-Scheinker syndrome, Finnish type amyloidosis, cerebral amyloid angiopathy, familial visceral amyloidosis, primary cutaneous amyloidosis prolactinoma, familial corneal amyloidosis, Parkinson's Disease, amyotrophic lateral sclerosis, cerebral amyloid angiopathy, frontotemporal lobar dementia, medullary thyroid carcinoma, and B2M amyloidosis. In some embodiments, the amyloidosis is a familial amyloidosis. In some embodiments, the amyloidosis is systemic amyloidosis.

In some embodiments, the disclosure provides for a method of reducing levels of an aggregate in a cell or tissue by treating the cell or tissue with any of the conjugates disclosed herein. In some embodiments, the disclosure provides for a composition comprising any of the conjugates disclosed herein and a pharmaceutically acceptable excipient.

DETAILED DESCRIPTION

The terms "linker" and "linkage" are used interchangeably and mean a chemical moiety comprising a covalent bond or a chain of atoms that covalently attaches, or is attached to, two different entities (e.g., any of the targeting moieties disclosed herein and any of the peptides disclosed herein).

"Linking moiety" means a chemically reactive group, substituent or moiety, e.g. a nucleophile or electrophile, capable of reacting with another molecule to form a linkage by a covalent bond.

The term "sequence similarity," in all its grammatical forms, refers to the degree of identity or correspondence between nucleic acid or amino acid sequences that may or may not share a common evolutionary origin. However, in common usage and in the instant application, the term "homologous," when modified with an adverb such as "highly," may refer to sequence similarity and may or may not relate to a common evolutionary origin.

"Percent (%) sequence identity" or "percent (%) identical" with respect to a reference peptide (or nucleotide) sequence is defined as the percentage of amino acid residues (or nucleic acids) in a candidate sequence that are identical to the amino acid residues (or nucleic acids) in the reference peptide (nucleotide) sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid (nucleic acid) sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

Numeric ranges disclosed herein are inclusive of the numbers defining the ranges, as well as any individual numbers or ranges present within the disclosed numeric range. For example, a disclosed range of "1-10" would include ranges such as "1-5", "2-6", "7-9", and "5-10"

The terms "a" and "an" include plural referents unless the context in which the term is used clearly dictates otherwise. The terms "a" (or "an"), as well as the terms "one or more," and "at least one" can be used interchangeably herein. Furthermore, "and/or" where used herein is to be taken as specific disclosure of each of the two or more specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Throughout this specification, the word "comprise" or variations such as "comprises" or "comprising" will be understood to imply the inclusion of a stated integer or groups of integers but not the exclusion of any other integer or group of integers. As used herein, the term "comprises" also encompasses the use of the narrower terms "consisting" and "consisting essentially of."

The term "consisting essentially of" is limited to the specified materials or steps and those that do not materially affect the basic and novel characteristics of the invention(s) disclosed herein.

"Amino acid" includes both natural amino acid and substituted amino acids. "Natural amino acid" refers to any of the commonly occurring amino acids as generally accepted in the peptide art and represent L-amino acids unless otherwise designated (with the exception of achiral amino acids such as glycine), including the canonical 20 amino acids encoded directly by the genetic code, as well as selenocysteine, selenomethionine, and ornithine. "Substituted amino acid" refers to an amino acid containing one or more additional chemical moieties that are not normally a part of the amino acid. Such substitutions can be introduced by a targeted derivatizing agent that is capable of reacting with selected side chains or terminal residues and via other art-accepted methods. For example, cysteinyl residues most commonly are reacted with alpha-haloacetates (and corresponding amines), such as chloroacetic acid or chloroacetamide, to give carboxymethyl or carboxyamidomethyl derivatives. Cysteinyl residues can also be derivatized by reaction with bromotrifluoroacetone, α-bromo-β-(5-imidazoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole. In some embodiments, carboxyl side groups (aspartyl or glutamyl) can be selectively modified by reaction with carbodiimides such as 1-cyclohexyl-3-(2-morpholinyl-(4-ethyl) carbodiimide or 1-ethyl-3 (4 azonia 4, 4-dimethylpentyl) carbodiimide. In some embodiments, aspartyl and glutamyl residues can be converted to asparaginyl and glutaminyl residues by reaction with ammonium ions. Glutaminyl and asparaginyl residues may be deamidated to the corresponding glutamyl and aspartyl residues. Alternatively, residues may be deamidated under mildly acidic conditions. Other modifications include hydroxylation of proline and lysine, phosphorylation of hydroxyl groups of seryl or theonyl residues, methylation of the alpha-amino groups of lysine, arginine and histidine side chains (see, e.g., T. E. Creighton, Proteins: Structure and Molecule Properties, W. H. Freeman & Co., San Francisco, pp. 79-86 (1983)), acetylation of the N-terminal amine, and amidation of C-terminal carboxyl groups. Blocking groups and/or activating groups may also be incorporated.

The terms “peptide”, “polypeptide”, “oligopeptide”, and “protein” are used interchangeably herein to refer to chains of amino acids of any length. The chain may be linear, branched, or cyclic, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labelling component. Also included within the definition are, for example, polypeptides containing one or more analogs of an amino acid (including, for example, unnatural amino acids, etc.), as well as other modifications known in the art. It is understood that the peptides can occur as single chains or associated chains.

1. The Peptides

In some embodiments, the conjugates comprise a peptide capable of activating an immune cell. In some embodiments, the peptide is capable of recruiting an immune cell. In some embodiments, the peptide is capable of competing with an Fc fragment of an IgG for binding to an Fc receptor. In some embodiments, the peptide is any of the peptides described in WO 2009/090268, which is incorporated by reference herein in its entirety.

In some embodiments, the peptide is less than 50, 45, 40, 35, 30, 25, 20, 15, or 10 amino acids in length. In some embodiments, the peptide is less than 25 amino acids in length. In some embodiments, the peptide is less than 20 amino acids in length. In some embodiments, the peptide is between 5-50, 10-50, 5-40, 10-40, 5-30, 10-30, 5-25, 10-25, 5-20, 10-20, or 15-25 amino acids in length.

The term peptide includes peptides containing post-translational modifications of the peptide, for example, glycosylations, acetylations, phosphorylations, and sulphations. In addition, protein fragments, analogs (including amino acids not encoded by the genetic code, e.g. homocysteine, ornithine, D-amino acids, and creatine), natural or artificial mutants or variants or combinations thereof, fusion proteins, derivatized residues (e.g. alkylation of amine groups, acetylations or esterifications of carboxyl groups) and the like are included within the meaning of peptide. By “modified” with reference to peptides, is meant a modification in one or more functional groups, for example any portion of an amino acid, the structure and/or location of a sugar or other carbohydrate, or other substituents of biomolecules, and can include without limitation chemical modifications (e.g., succinylation, acylation, the structure and/or location of disulfide bonds), as well as noncovalent binding (e.g., of a small molecule, including a drug).

A peptide according to an embodiment of the present invention may be used herein to refer to constrained (i.e. having some element allowing cyclisation between two backbone termini, two side chains, or one of the termini and a side chain, as for example, amide or disulfide bonds) or unconstrained (e.g. linear) amino acid sequences of less than about 50 amino acid residues, such as less than about 40, 30, 20 or 10 amino acid residues. This list may also include oligomers, such as 3, 4 or 5 peptides linked together or dimers comprising 2 peptides linked together by means of a peptide linker, for example. In particular embodiments, the peptides are between about 10 and about 30 amino acid residues, and in more particular embodiments, 16 to 18 amino acid residues. However, on reading the present disclosure, it will be apparent to the skilled person that it is not the length of a particular peptide that is required but its ability to bind to an Fc receptor (e.g., FcγRI) and compete with the binding of IgG. For example, amino acid sequences of 5, 6, 7, 8, 9, 10, 11, 12, 13, 14, 15, 16, 17, 18, 19, 20, 21, 22, 23, 24 and 25 amino acid residues are contemplated to be peptide compounds within the context of the present invention. A dimeric peptide may have an amino acid sequence comprising two peptide amino acid sequences linked by a linker. The linker may comprise an amino acid sequence of less than about 10 amino acid residues, such as 9, 8, 7, 6, 5, 4 or 3 amino acid residues. The linker amino acid residues may be of a single amino acid or combinations of different amino acids. For example, combinations of glycine (G) and serine (S) may be used. Alternatively, the linker may comprise residues of glycine, serine or lysine (K) only.

A peptide of the invention that is able to mimic biological activity of an Fc fragment, such as effector function may be termed a ‘Fc mimetic peptide’. Effector function of an Fc fragment as encompassed by, but not limited by, the present invention comprises phagocytosis, CDC and/or ADCC. In some embodiments, the biologically active peptide binds to an Fc receptor, e.g., a Fcγ receptor. In some embodiments, such a peptide competes with the Fc fragment of IgG for binding to Fc receptor (e.g., a Fcγ receptor) and therefore binds to the same or an overlapping binding site on the Fc receptor (e.g., Fcγ receptor) as the Fc fragment. Present in a complex form (multimeric), which may include dimers and oligomers, an Fc mimetic peptide may trigger effector functions. Present in soluble form (monomeric), an Fc mimetic peptide can inhibit effector functions. In some embodiments, these peptides in soluble form may be able to activate effector functions if the $IC_{50}$ concentration of the soluble form required to inhibit the effector function is lower than 10-20 μM.

A peptide that is unable to mimic the effector functions of an Fc fragment of an IgG to an Fcγ receptor, namely to trigger effector functions in multimeric form and inhibit effector functions in soluble form may be referred to as ‘Fc an non-mimetic peptide’. Using this terminology, four groups of peptides may be defined: i) the first group comprises a peptide that competes with the Fc fragment for binding to the Fc receptor (e.g., Fcγ receptor) and therefore binds to the same binding site on the Fc receptor (e.g., Fcγ receptor) as the Fc fragment. However, such peptides cannot activate effector functions in a complexed form but can activate effector functions when in soluble form. In some embodiments, these peptides may have lost their ability to trigger effector functions if the $IC_{50}$ concentration of the soluble form required to inhibit the effector function is higher than 10-20 μM and hence the avidity of the complexed peptide is sufficiently low. ii) The second group comprises a peptide that competes with the Fc fragment of an IgG for binding to the Fc receptor (e.g., Fcγ receptor) and therefore binds to the same binding site on the Fc receptor (e.g., Fcγ receptor) as the Fc fragment. In some embodiments, this peptide can activate effector functions when in a dimeric as well as when in a complexed form i.e. as a soluble cyclic peptide dimer. Such peptides may also be known as committed agonists. iii) The third group comprises a peptide that does not compete with the Fc fragment of an IgG for binding to the Fc receptor (e.g., Fcγ receptor). These peptides however can activate the Fc receptor (e.g., Fcγ receptor) when in complexed form (Berntzen et al, 2006). iv) The fourth group comprises a peptide that does not compete with the Fc fragment of an IgG for binding to the Fc receptor (e.g., Fcγ receptor) but is able to bind to the Fc receptor (e.g., Fcγ receptor) at a site distinct from the Fc binding site. These peptides cannot activate or inhibit effector functions in complexed or soluble form. These peptides may have an affinity and avidity that is too high to activate effector function.

In some embodiments, any of the peptides disclosed herein may comprise both naturally and non-naturally occurring amino acid sequences. By non-naturally occurring is meant that the amino acid sequence is not found in nature. In some embodiments, non-naturally occurring amino acid sequences have between about 10 and 30 amino acid residues, alternatively about 20 amino acid residues. These include peptides, peptide analogs, peptoid and peptidomimetics containing naturally as well as non-naturally occurring amino acids. In a specific aspect, the peptides of the invention comprise amino acid residues consisting of only naturally occurring amino acids.

A C-terminal region of an immunoglobulin heavy chain that also comprises the hinge region between the two constant domains CH1 and CH2 may be referred to as a 'Fc fragment.' This fragment of the C-terminal region may be a native sequence Fc fragment or a variant Fc fragment. Although the boundaries of the Fc fragment of an immunoglobulin heavy chain can vary, the human IgG heavy chain Fc fragment is usually defined to stretch from an amino acid residue at position 231 to the carboxyl-terminus thereof. With the upper and core hinge, the 'Fc fragment' starts from position 216 (EU nomenclature according to Rabat (1987, 1991)). The Fc fragment of an immunoglobulin generally comprises two constant domains, CH2 and CH3. The CH2 domain of a human IgG Fc fragment usually extends from about amino acid 231 to about amino acid 340. The CH3 domain of a human IgG Fc fragment usually extends from about amino acid 341 to about amino acid residue 447 of a human IgG (i.e. comprises the residues C-terminal to a CH2 domain). In some embodiments of the present invention, the variant IgG Fc fragment may be selected from IgG1, IgG2, IgG3 or IgG4. In particular embodiments, the IgG Fc fragment of IgG1. In some embodiments, the IgG1 Fc may be written in the alternative as Fcγ1. A 'hinge fragment' is generally defined as stretching from Glu 216 to Pro 230 of human IgG1, or the equivalent positions in IgG2, IgG3 or IgG4 (Burton, 1985). A functional Fc fragment possesses an effector function of a native sequence Fc fragment for example: C1q binding, CDC, Fc receptor binding, phagocytosis, endocytosis of opsonized particles, antigen presentation, release of inflammatory mediators (e.g. IL-6, TNFα, IL-1), cellular cooperation, superoxide burst, ADCC, down regulation of cell surface receptors (e.g. B cell receptor), etc. Effector function of an Fc fragment as encompassed by, but not limited by the present invention comprises phagocytosis, CDC and/or ADCC.

As is generally known in the art, an Fcγ receptor (FcγR) is a receptor that binds an IgG antibody and includes receptors of the FcγRI, FcγRII and FcγRIII subclasses, including allelic variants and alternatively spliced forms of these receptors. FcγRII receptors include FcγRIIa (an activating receptor) and FcγRIIb (an inhibiting receptor), which have similar amino acid sequences that differ primarily in the cytoplasmic domains thereof. Fc receptors are reviewed in Ravetch and Kinet (1991, Annu. Rev. Immunol 9: 457-92); Capel et al., (1994, Immunomethods 4: 25-34); and de Haas et al., (1995, J. Lab. Clin. Med. 126: 330-41).

A peptide according to an embodiment of the present invention may be obtained from a library of peptides that are able to bind to an Fcγ receptor such as FcγRI. The library may be displayed on particles or molecular complexes, e.g. replicable genetic packages, such as yeast, bacterial or bacteriophage (e.g. T7) particles, viruses, cells or covalent, ribosomal, microbead or other in vitro display systems, each particle or molecular complex containing nucleic acid encoding the peptide. Phage display is described in WO92/01047 and e.g. U.S. Pat. Nos. 5,969,108, 5,565,332, 5,733,743, 5,858,657, 5,871,907, 5,872,215, 5,885,793, 5,962,255, 6,140,471, 6,172,197, 6,225,447, 6,291,650, 6,492,160 and 6,521,404, each of which is herein incorporated by reference in their entirety.

Following selection of peptides of the invention able to bind an FcγRI receptor and displayed on bacteriophage or other library particles or molecular complexes, nucleic acid may be taken from a bacteriophage or other particle or molecular complex displaying a said selected peptide. Such nucleic acid may be used in subsequent production of a peptide by expression from nucleic acid with the sequence of nucleic acid taken from a bacteriophage or other particle or molecular complex displaying a said peptide.

In some embodiments, a peptide of the invention in soluble form can bind to the FcγRI without eliciting an effector response. In some embodiments, in order to activate the receptor it is necessary for receptor clustering to occur.

In some embodiments, ability to bind FcγRI may be further tested, also ability to compete with e.g. an Fc fragment of an IgG for binding to FcγRI. In some embodiments, a peptide according to the present invention may bind FcγRI with the affinity of a functional Fc fragment or with an affinity that is better or lower, as measured by, for example, BIACORE.

Binding affinity of different peptides can be compared under appropriate conditions.

The techniques required to make substitutions within amino acid sequences of peptides of the invention are available in the art. Variant sequences may be made, with substitutions that may or may not be predicted to have a minimal or beneficial effect on effector function, and tested for ability to bind Fc receptors and/or for any other desired property.

In some embodiments, the peptide comprises a sequence that has at least 60%, 70%, 80%, 85%, 90%, 91%, 92%, 93%, 94%, 95%, 96%, 97%, 98% or 99% amino acid sequence homology with a sequence of any one of SEQ ID Nos: 1-21, or a functional fragment thereof. In some embodiments, the peptide comprises a sequence that has at least 60%, 70%, 80%, 85%, 90%, 91%, 92%, 93%, 94%, 95%, 96%, 97%, 98% or 99% amino acid sequence identity with a sequence of any one of SEQ ID Nos: 1-21, or a functional fragment thereof. In the context of any of the peptides disclosed herein, a "functional fragment thereof" is defined as being capable of binding to and/or activating an Fc receptor (e.g., hFcγRI).

In some embodiments, the peptide comprises an amino acid sequence of TX2CXXζPXLLGCφXE (SEQ ID NO: 1); wherein X is any amino acid, ζ is a hydrophobic residue and φ is an acidic amino acid. In some embodiments, the peptide binds specifically to hFcγRI and does not exhibit cross-reactivity with hFcγRII or hFcγRIII. In some embodiments, the peptide comprises the amino acid sequence of AQVNSCLLLPNLLGC (SEQ ID NO: 2). In some embodiments, the peptide comprises the amino acid sequence of AQVN- SCLLLPNLLGCGDDK (SEQ ID NO: 3). In some embodiments, the peptide comprises the amino acid sequence of any one of:

```
                                        (SEQ ID NO: 4)
TDTCLMLPLLLGCDEE

                                        (SEQ ID NO: 5)
DPICWYFPRLLGCTTL

                                        (SEQ ID NO: 6)
WYPCYIYPRLLGCDGD

                                        (SEQ ID NO: 7)
GNICMLIPGLLGCSYE

                                        (SEQ ID NO: 8)
VNSCLLLPNLLGCGDD

                                        (SEQ ID NO: 9)
TPVCILLPSLLGCDTQ

                                       (SEQ ID NO: 10)
TVLCSLWPELLGCPPE

                                       (SEQ ID NO: 11)
TFSCLMWPWLLGCESL

                                       (SEQ ID NO: 12)
FGTCYTWPWLLGCEGF

                                       (SEQ ID NO: 13)
SLFCRLLLTPVGCVSQ

                                       (SEQ ID NO: 14)
HLLVLPRGLLGCTTLA

                                       (SEQ ID NO: 15)
TSLCSMFPDLLGCFNL

                                       (SEQ ID NO: 16)
SHPCGRLPMLLGCAES

                                       (SEQ ID NO: 17)
TSTCSMVPGPLGAVSTW

                                       (SEQ ID NO: 18)
KDPCTRWAMLLGCDGE

                                       (SEQ ID NO: 19)
IMTCSVYPFLLGCVDK

                                       (SEQ ID NO: 20)
IHSCAHVMRLLGCWSR

                                       (SEQ ID NO: 21)
AQVNSCLLLPNLLGCSYEKKKKKEYSCGLLNPLLLCNVQA
```

In some embodiments, one or more of the amino acids in the peptide are modified to reduce proteolysis. In some embodiments, one or more of the amino acid residues in the peptide are methylated. In some embodiments, one or more of the asparagine amino acid residues in the peptide (if the peptide comprises one or more asparagine amino acid residues) are methylated. In some embodiments, one or more of the leucine amino acid residues in the peptide (if the peptide comprises one or more leucine amino acid residues) are methylated. In some embodiments, the asparagine residue at the amino acid position corresponding to position 11 of SEQ ID NO: 2 or 3 is methylated. In some embodiments, the leucine residue at the amino acid position corresponding to position 13 of SEQ ID NO: 2 or 3 is methylated.

Orthologs of proteins are typically characterized by possession of greater than 75% sequence identity counted over the full-length alignment with the amino acid sequence of specific protein using ALIGN set to default parameters. Proteins with even greater similarity to a reference sequence will show increasing percentage identities when assessed by this method, such as at least 80%, at least 85%, at least 90%, at least 92%, at least 95%, or at least 98% sequence identity. In addition, sequence identity can be compared over the full length of specific domain (s) of the disclosed peptides. When significantly less than the entire sequence is being compared for sequence identity, homologous sequences will typically possess at least 80% sequence identity over short windows of 10-20 amino acids, and may possess sequence identities of at least 85%, at least 90%, at least 95%, or at least 99% depending on their similarity to the reference sequence. Sequence identity over such short windows can be determined using LFASTA; methods are described at the NCSA Website.

Particular variants may include one or more amino acid sequence alterations (addition, deletion, substitution and/or insertion of an amino acid residue) as compared to any of SEQ ID NOs: 1-21. In some embodiments, the peptide has 1, 2, 3, 4, 5, 6, 7, 8, 9, 10, 11, 12, 13, 14, or 15 amino acid alterations as compared to any of SEQ ID NOs: 1-21. In some embodiments, the peptide having 1 or more amino acid alterations as compared any of SEQ ID NOs: 1-21 is capable of still binding to an Fc receptor (e.g., to an Fc receptor such as FcγRI).

In some embodiments, the peptide has 1, 2, 3, 4, 5, 6, 7, 8, 9 or 10 conservative amino acid substitutions as compared to any of SEQ ID NOs: 1-21. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a peptide (e.g., the peptide's ability to bind to an Fc receptor such as FcγRI). In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. In particular embodiments, conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445. A "moderately conservative" replacement is any change having a nonnegative value in the PAM250 log-likelihood matrix.

In some embodiments, one or more amino acid residues in any of the peptide sequences disclosed herein are replaced with a non-naturally occurring or non-standard amino acid, modifying one or more amino acid residue into a non-naturally occurring or non-standard form, or inserting one or more non-naturally occurring or non-standard amino acid into the sequence. Examples of numbers and locations of alterations in sequences of the invention are described elsewhere herein. Naturally occurring amino acids include the 20 "standard" L-amino acids identified as G, A, V, L, I, M, P, F, W, S, T, N, Q, Y, C, K, R, H, D, E by their standard single-letter codes. In some embodiments, any of the peptides disclosed herein comprises one or more non-naturally occurring amino acids. Non-standard amino acids include any other residue that may be incorporated into a peptide backbone or result from modification of an existing amino acid residue. Non-standard amino acids may be naturally occurring or non-naturally occurring. Several naturally occurring non-standard amino acids are known in the art, such as 4-hydroxyproline, 5-hydroxylysine, 3-methylhistidine, N-acetylserine, etc. (Voet & Voet, Biochemistry, 2nd Edition, (Wiley) 1995). Those amino acid residues that are derivatised at their N-alpha position will only be located at the N-terminus of an amino-acid sequence. Normally in the present invention an amino acid is an L-amino acid, but it may be a D-amino acid. Alteration may therefore comprise modifying an L-amino acid into, or replacing it with, a D-amino acid. Methylated, acetylated and/or phosphorylated forms of amino acids are also known, and amino acids in the present invention may be subject to such modification.

Amino acid sequences in antibody domains and peptides of the invention may comprise non-natural or non-standard amino acids described above. Non-standard amino acids (e.g. D-amino acids) may be incorporated into an amino acid sequence during synthesis, or by modification or replacement of the "original" standard amino acids after synthesis of the amino acid sequence.

In some embodiments, use of non-standard and/or non-naturally occurring amino acids increases structural and functional diversity, and can thus increase the potential for achieving desired properties in a peptide of the invention. Additionally, D-amino acids and analogues have been shown to have better pharmacokinetic profiles compared with standard L-amino acids, owing to in vivo degradation of peptides having L-amino acids after administration to an animal e.g. a human.

In some embodiments, at least 50%, 60%, 70%, 80%, 85%, 90%, 95% or 100% of the amino acids in the peptide are D-amino acids. In particular embodiments, all of the amino acids in the peptide are D-amino acids. In some embodiments, the disclosure provides for a peptide that comprises an amino acid sequence that is in the reverse order of any of the amino acid sequences disclosed herein or that is in the reverse order of an amino acid sequence portion of an antibody that is capable of binding to an Fc receptor (e.g., FcγRI). In some embodiments, the disclosure provides for a "retro-inverse" peptide in which all of the amino acids in the peptide are D-amino acids and that comprises an amino acid sequence that is in the reverse order of any of the amino acid sequences disclosed herein or that is in the reverse order of an amino acid sequence portion of an antibody that is capable of binding to an Fc receptor (e.g., FcγRI). A "retro-inverse" peptide may be desirable because it would be less likely to be cleaved by proteases present in a subject that had been administered the peptide or a conjugate comprising the peptide. Peptides of the invention can be further modified or derivatized to contain additional nonproteinaceous moieties that are known in the art and readily available. Such derivatives may improve the solubility, absorption and/or biological half-life of the compounds. The moieties may alternatively eliminate or attenuate any undesirable side-effect of the compounds.

Exemplary derivatives include compounds in which: the compound is cross-linked or is rendered capable of cross-linking between molecules. For example, the peptide portion may be modified to contain one Cys residue and thereby be able to form an intermolecular disulfide bond with a like molecule. The compound may also be cross-linked through its C-terminus.

In some embodiments, the N-terminus may be acylated or modified to a substituted amine. Exemplary N-terminal derivative groups include —NRR1 (other than —NH2), —NRC(O)R1, —NRC(O)OR1, —NRS(O)2R1, —NHC(O)NHR1, succinimide, or benzyloxycarbonyl-NH—(CBZ—NH—), wherein R and R1 are each independently hydrogen or lower alkyl and wherein the phenyl ring may be substituted with 1 to 3 substituents selected from the group consisting of C1-C4 alkyl, C1-C4 alkoxy, chloro, and bromo.

In some embodiments, the C-terminus may be esterified or amidated. For example, methods described in the art may be used to add $(NH—CH_2—CH_2—NH_2)_2$ to peptides of this invention. Likewise, methods described in the art may be used to add-NH2 to peptides of this invention. Exemplary C-terminal derivative groups include, for example, —C(O)R2 wherein R2 is lower alkoxy or —NR3R4 wherein R3 and R4 are independently hydrogen or C1-C8 alkyl (e.g. C1-C4 alkyl).

In some embodiments, a disulfide bond may be replaced with another, more stable, cross-linking moiety (e.g., an alkylene). See, for example: Bhatnagar et al. (1996), J. Med. Chem. 39: 3814 9; Alberts et al. (1993) Thirteenth Am. Pep. Symp., 357-9.

In some embodiments, one or more individual amino acid residues may be modified. Various derivatizing agents are known to react specifically with selected side chains or terminal residues, as described in detail below:

In some embodiments, lysinyl residues and amino terminal residues may be reacted with succinic or other carboxylic acid anhydrides, which reverse the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

In some embodiments, arginyl residues may be modified by reaction with any one or combination of several conventional reagents, including phenylglyoxal, 2, 3-butanedione, 1, 2-cyclohexanedione, and ninhydrin. Derivatization of arginyl residues requires that the reaction be performed in alkaline conditions because of the high pKa of the guanidine functional group. Furthermore, these reagents may react with the groups of lysine as well as the arginine epsilon-amino group.

Specific modification of tyrosyl residues has been studied extensively, with particular interest in introducing spectral labels into tyrosyl residues by reaction with aromatic diazonium compounds or tetranitromethane. N-acetylimidazole; and tetranitromethane may be used to form 0-acetyl tyrosyl species and 3-nitro derivatives, respectively.

In some embodiments, carboxyl sidechain groups (aspartyl or glutamyl) may be selectively modified by reaction with carbodiimides (R'—N═C═N— R') such as 1-cyclohexyl-3-(2-morpholinyl-(4-ethyl) carbodiimide or 1-ethyl-3-(4-azonia-4, 4-dimethylpentyl) carbodiimide. Furthermore, aspartyl and glutamyl residues may be converted to asparaginyl and glutaminyl residues by reaction with ammonium ions.

In some embodiments, glutaminyl and asparaginyl residues may be deamidated to the corresponding glutamyl and aspartyl residues. Alternatively, these residues are deamidated under mildly acidic conditions. Either form of these residues falls within the scope of this disclosure. Cysteinyl residues can be replaced by amino acid residues or other moieties either to eliminate disulfide bonding or, conversely, to stabilize cross-linking. See, e.g., Bhatnagar et al. (1996), J. Med. Chem. 39: 3814-9.

Derivatization with bifunctional agents is useful for cross-linking the peptides of the invention or their functional derivatives to a water-insoluble support matrix or to other macromolecular vehicles. Commonly used cross-linking agents include, e.g., 1, 1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1, 8-octane. Derivatizing agents such as methyl-3-[(p-azidophenyl)dithio] propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

In some embodiments, carbohydrate (oligosaccharide) groups may conveniently be attached to sites that are known to be glycosylation sites in proteins. In some embodiments, O-linked oligosaccharides are attached to serine (Ser) or threonine (Thr) residues while N-linked oligosaccharides are attached to asparagine (Asn) residues when they are part of the sequence Asn-X-Ser/Thr, where X can be any amino acid except proline. In some embodiments, X is one of the 19 naturally occurring amino acids other than proline. The structures of N-linked and O-linked oligosaccharides and the sugar residues found in each type are different. One type of sugar that is commonly found on both is N-acetylneuraminic acid (referred to as sialic acid). Sialic acid is usually the terminal residue of both N-linked and O-linked oligosaccharides and, by virtue of its negative charge, may confer acidic properties to the glycosylated compound.

Such site(s) may be incorporated in the linkers contemplated for the peptides of the invention and, in some embodiments, are glycosylated by a cell during recombinant production of the peptide compounds (e.g., in mammalian cells such as CHO, BHK, COS). However, such sites may further be glycosylated by synthetic or semi-synthetic procedures known in the art.

Other possible modifications include hydroxylation of proline and lysine, phosphorylation of hydroxyl groups of seryl or threonyl residues, oxidation of the sulphur atom in Cys, methylation of the alpha-amino groups of lysine, arginine, and histidine side chains. Creighton, Proteins: Structure and Molecule Properties (W. H. Freeman & Co., San I Francisco), pp. 79-86 (1983).

In particular embodiments, the moieties suitable for derivatization of the peptides are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1, 3, 6-trioxane, ethylene/maleic anhydride copolymer, polyaminoacids (either homopolymers or random copolymers), and dextran or poly(n-vinyl pyrrolidone) polyethylene glycol, propropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The polymer may be linked to the peptide in the manner set forth in: U.S. Pat. Nos. 4,640,835, 4,496,689, 4,301,144, 4,670,417, 4,791,192 or 4,179,337. WO 93/00109 also describes methods of linking amino acid residues in peptides to PEG molecules. The number of polymers attached to the peptide may vary, and if more than one polymers are attached, they can be the same or different molecules. In general, the number and/or type of polymers used for derivatization can be determined based on considerations including, but not limited to, the particular properties or functions of the peptide to be improved or whether it will be used in a therapy under defined conditions, for example.

In an alternative embodiment, peptides of the invention can be further modified to contain a serum carrier protein in order to extend the half life in vivo. The serum carrier protein may be a naturally occurring serum carrier protein or a fragment thereof. Particular examples include thyroxine-binding protein, transthyretin, al-acid glycoprotein, transferrin, fibrinogen and especially, albumin, together with fragments thereof. In some embodiments, the carrier proteins are of human origin. Where desired each may have one or more additional or different amino acids to the naturally occurring sequence providing that the resulting sequence is functionally equivalent with respect to half-life. Fragments include any smaller part of the parent protein that retains the carrier function of the mature sequence. The peptide and carrier protein components may be directly or indirectly covalently linked. Indirect covalent linkage is intended to mean that an amino acid in a peptide is attached to an amino acid in a carrier protein through an intervening chemical sequence, for example a bridging group. Particular bridging groups include for example aliphatic, including peptide. Direct covalent linkage is intended to mean that an amino acid in a peptide is immediately attached to an amino acid in a carrier protein without an intervening bridging group. Particular examples include disulphide [—S—S—] and amide [—CONH—] linkages, for example when a cysteine residue in one component is linked to a cysteine residue in another through the thiol group in each, and when the C-terminal acid function of one component is linked to the N-terminal amine of the other.

In addition to any of the targeting moieties described herein, any of the peptides disclosed herein may also be labelled with a detectable or functional label. Thus, a peptide can be present in the form of a peptide conjugate so as to obtain a detectable and/or quantifiable signal. A peptide conjugate may comprise a peptide of the invention conjugated with a detectable or functional label. A label can be any molecule that produces or can be induced to produce a signal, including but not limited to fluorescers, radiolabels, enzymes, chemiluminescers or photosensitizers. Thus, binding may be detected and/or measured by detecting fluorescence or luminescence, radioactivity, enzyme activity or light absorbance.

Suitable labels include, by way of illustration and not limitation,

- enzymes, such as alkaline phosphatase, glucose-6-phosphate dehydrogenase ("G6PDH"), alpha-D-galactosidase, glucose oxydase, glucose amylase, carbonic anhydrase, acetylcholinesterase, lysozyme, malate dehydrogenase and peroxidase e.g. horseradish peroxidase;
- Fluorescent label/pigment/stain;
  - fluorescent labels or fluorescers, such as fluorescein and its derivatives, fluorochrome, rhodamine compounds and derivatives, GFP (GFP for "Green Fluorescent Protein"), dansyl, umbelliferone, phycoerythrin, phycocyanin, allophycocyanin, o-phthaldehyde, and fluorescamine; fluorophores such as lanthanide cryptates and chelates e.g. Europium etc (Perkin Elmer and Cis Biointernational), -chemiluminescent labels or chemiluminescers, such as isoluminol, luminol and the dioxetanes;

bio-luminescent labels, such as luciferase and luciferin;

sensitizers;

coenzymes;

enzyme substrates;

radiolabels including but not limited to bromineW, carbon14, cobalt57, fluorineδ, gallium67, gallium 68, hydrogen3 (tritium), indium111, indium 113m, iodine123m, iodine125, iodine126, iodine131, iodine133, mercury107, mercury203, phosphorous32, rhenium99m, rhenium101, rhenium105, ruthenium95, ruthenium97, ruthenium103, ruthenium105, scandium47, selenium75, sulphur35, technetium99, technetium99m, tellurium121m, tellurium122m, tellurium125m, thulium165, thulium167, thulium168, yttrium199 and other radiolabels mentioned herein;

particles, such as latex or carbon particles; metal sol; crystallite; liposomes; cells, etc., which may be further labelled with a dye, catalyst or other detectable group; -molecules such as biotin, digoxygenin or 5-bromodeoxyuridine;

toxin moieties, such as for example a toxin moiety selected from a group of Pseudomonas exotoxin (PE or a cytotoxic fragment or mutant thereof), Diphtheria toxin or a cytotoxic fragment or mutant thereof, a botulinum toxin A, B, C, D, E or F, ricin or a cytotoxic fragment thereof e.g. ricin A, abrin or a cytotoxic fragment thereof, saporin or a cytotoxic fragment thereof, pokeweed antiviral toxin or a cytotoxic fragment thereof and bryodin 1 or a cytotoxic fragment thereof.

Suitable enzymes and coenzymes are disclosed in Litman, et al., U.S. Pat. No. 4,275,149, and Boguslaski, et al., U.S. Pat. No. 4,318,980, each of which are herein incorporated by reference in their entireties. Suitable fluorescers and chemiluminescers are disclosed in Litman, et al., U.S. Pat. No. 4,275,149, which is incorporated herein by reference in its entirety. Labels further include chemical moieties, such as biotin that may be detected via binding to a specific cognate detectable moiety, e.g. labelled avidin or streptavidin. Detectable labels may be attached to peptides of the invention using conventional chemistry known in the art, or by gene fusion.

In some embodiments, the disclosure provides for a peptide that is an antibody fragment capable of binding to an Fc receptor (e.g., an FcγRI). It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward et al 1989, McCafferty et al 1990, Holt et al 2003), which consists of a VH or a VL domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al 1988, Huston et al 1988); (viii) bispecific single chain Fv dimers (PCT/US92/09965) and (ix) "diabodies", multivalent or multispecific fragments constructed by gene fusion (WO94/13804; Hollinger et al 1993). Fv, scFv or diabody molecules may be stabilized by the incorporation of disulphide bridges linking the VH and VL domains (Reiter et al 1996). Minibodies comprising a scFv joined to a CH3 domain may also be made (Hu et al 1996). Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue (s) of the constant domains bear a free thiol group. Antibody fragments that comprise an antibody antigen-binding site include, but are not limited to, molecules such as Fab, Fab', Fab'-SH, scFv, Fv, dAb and Fd. Various other antibody molecules including one or more antibody antigen-binding sites have been engineered, including for example Fab2, Fab3, diabodies, triabodies, tetrabodies and minibodies. Antibody molecules and methods for their construction and use are described in Hollinger & Hudson (2005).

2. The Targeting Moiety

In some embodiments, any of the peptides disclosed herein is conjugated to one or more targeting moieties.

In some embodiments, the targeting moiety targets protein aggregates. In some embodiments, the protein aggregates comprise aggregates of any one of the following proteins: alpha-synuclein, tau, amyloid beta, TDP-43, SOD1, FUS, TDP-43, prion protein, immunoglobulin light chain, transthyretin, fibrinogen, collagen, islet amyloid polypeptide, lysozyme, calcitonin, serum amyloid A protein, LECT2, amylin, gelsolin, fibrinogen A, prolactin, keratoepithelin, and $\beta_2$-microglobin.

In some embodiments, the targeting moiety targets lipid aggregates. In some embodiments, the lipid aggregates are cholesterol aggregates.

In some embodiments, the targeting moiety targets polysaccharide aggregates. In some embodiments, the targeting moiety targets glycogen aggregates.

In some embodiments, the targeting moiety is a peptide. In some embodiments, the targeting moiety is a nucleic acid. In some embodiments, the targeting moiety is a lipid. In some embodiments, the targeting moiety is a polysaccharide. In particular embodiments, the targeting moiety is a dye, or a derivative thereof.

In some embodiments, the targeting moiety is a small molecule. In some embodiments, the targeting moiety is less than 1000 g/mol, less than 900 g/mol, less than 800 g/mol, less than 700 g/mol, less than 800 g/mol, less than 700 g/mol, less than 600 g/mol, less than 500 g/mol, less than 400 g/mol, less than 300 g/mol, less than 200 g/mol, or less than 100 g/mol in size. In particular embodiments, the targeting moiety is less than 500 g/mol in size. In particular embodiments, the targeting moiety is less than 400 g/mol in size.

In particular embodiments, the targeting moiety is a dye, or a derivative thereof. As used herein, a "dye" is defined as being a compound that is, or is derived from, a natural or synthetic substance used to add a color to or change the color of protein, polysaccharides, lipid, metals and/or nucleotides. In some embodiments, the dye may be used to stain cells or components thereof. The skilled worker would understand what classifies as a dye/stain. In some embodiments, the dye is a compound capable of binding to a protein, polysaccharide, lipid, metal, and/or nucleotide to facilitate visualization of the protein, polysaccharide, lipid, metal, and/or nucleotide. In preferred embodiments, the dye binds to an aggregate or a component present in an aggregate. In some embodiments, the dye binds to protein, polysaccharide, lipid, metal, and/or nucleotide in an aggregate. In some embodiments, the targeting moiety is a derivative of a dye that retains the ability to bind to a specific target (e.g., proteins, peptides, polysaccharides, nucleotides, lipids or aggregates thereof), but lacks or has a modified staining capability as compared to the dye from which the derivative was derived.

In some embodiments, the dye binds to amyloid. In some embodiments, the dye is selected from the group consisting of: a thioflavin, pentamer formyl thiophene acetic acid (pFTAA), heptamer formyl thiophene acetic acid (hFTAA), Congo Red, crystal violet, 1-amino-8-naphtalene sulphonate (ANS), 4-(dicyanovinyl)-julolidine (DCVJ), aminobenzanthrone, Methoxy XO4, thiazin red, Pittsburgh B, ProteoStat® and amyloid-binding derivatives thereof. In some embodiments, the thioflavin is thioflavin T, or an amyloid-binding derivative thereof. In some embodiments, the amyloid-binding derivative of thioflavin T comprises the formula of Compound I:

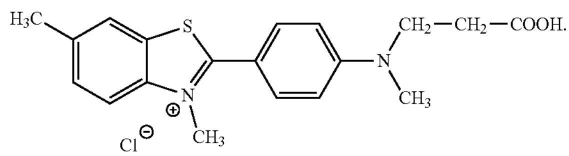 [SMILES: Cc1ccc2c(c1)sc(-c1ccc(N(C)CCC(=O)O)cc1)[n+]2C ; [Cl-]]

In some embodiments, the amyloid comprises any one or more of the following proteins: alpha-synuclein, tau, amyloid beta, TDP-43, SOD1, FUS, C79ORF, TDP-43, prion protein, immunoglobulin light chain, transthyretin, fibrinogen, collagen, islet amyloid polypeptide, lysozyme, calcitonin, serum amyloid A protein, LECT2, amylin, gelsolin, fibrinogen A, prolactin, keratoepithelin, and $\beta_2$-microglobin, or fragments or derivatives thereof. In some embodiments, the amyloid comprises lysozyme.

In some embodiments, the dye binds to cholesterol. In some embodiments, the dye is filipin, or a cholesterol-binding derivative thereof.

In some embodiments, the dye binds to collagen. In some embodiments, the dye is sinus red, Col-F, Oregon Green 488, Picrosirius red. Light Green SF yellowish, Fast Green FCF, methyl blue, water blue, aniline blue, and collagen-binding derivatives thereof.

In some embodiments, the dye binds polysaccharide aggregates. In some embodiments, the dye binds glycogen aggregates. In some embodiments, the dye is selected from the group consisting of carmine, periodic acid, alcian blue, and Dimethyl methylene blue.

In some embodiments, the dye binds nucleotide aggregates. In some embodiments, the dye binds to RNA aggregates. In some embodiments, the dye binds DNA aggregates. In some embodiments, the dye binds to polynucleotides having expanded CUG, CAG, CCUG, CCG or CGG repeats.

In some embodiments, the targeting moiety has been modified to facilitate conjugation to the peptide. In some embodiments, the targeting moiety has been modified such that it includes a carboxyl group. In some embodiments, the carboxyl group of the targeting moiety is bonded to the amino terminus of the peptide. In some embodiments, the targeting moiety has been modified such that it includes an amino group. In some embodiments, the amino group of the targeting moiety is bonded to the carboxy terminus of the peptide. In some embodiments, the targeting moiety is conjugated to the peptide by means of a linker. In some embodiments, the linker is selected from the group consisting of non-cleavable linker, hydrazone linkers, thioether linkers, disulfide linkers, peptide linkers and β-glucuronide linkers. In certain such embodiments, the linker is rigid.

3. The Conjugates

In some embodiments, any of the peptides disclosed herein is fused to any of the targeting moieties disclosed herein to generate any of the conjugates disclosed herein.

In some embodiments, any of the targeting moieties disclosed herein (e.g., any of the dyes disclosed herein) are conjugated directly to any of the peptides disclosed herein (e.g., in the absence of a linker). In some embodiments, any of the targeting moieties disclosed herein (e.g., any of the dyes disclosed herein) are conjugated to any of the peptides disclosed herein by means of a linker or linkage moiety. In some embodiments, any of the targeting moieties disclosed herein (e.g., any of the dyes disclosed herein) are covalently attached by linkages to the peptide. In some embodiments, the linker is rigid. In alternative embodiments, the linker is flexible. In preferred embodiments, the linker should not (i) inhibit and/or adversely affect the aggregate-targeting properties of the targeting moiety (e.g., dye), or (ii) inhibit and/or adversely affect the ability of the peptide to compete with an Fc fragment of an IgG for binding to an Fc receptor.

In some embodiments, the targeting moiety includes a reactive linking group, "linking moiety", at one of the substituent positions for covalent attachment of the targeting moiety (e.g., dye) to a peptide. Linking moieties capable of forming a covalent bond are typically electrophilic functional groups capable of reacting with nucleophilic molecules, such as alcohols, alkoxides, amines, hydroxylamines, and thiols. Examples of electrophilic linking moieties include succinimidyl ester, isothiocyanate, sulfonyl chloride, sulfonate ester, silyl halide, 2, 6-dichlorotriazinyl, pentafluorophenyl ester, phosphoramidite, maleimide, iodoacetamide, haloacetyl, epoxide, alkylhalide, allyl halide, aldehyde, ketone, acylazide, and anhydride. In some embodiments, a linking moiety is an N-hydroxysuccinimidyl ester (NHS) of a carboxyl group substituent on a targeting moiety (e.g., dye).

In some embodiments, the linking moiety is a phosphoramidite reagent any of the dyes disclosed herein. Other activating and coupling reagents include TBTU (2-(1H-benzotriazo-1-yl)-1-1,3,3-tetramethyluronium hexafluorophosphate), TFFH(N,N',N",N'"-tetramethyluronium 2-fluoro-hexafluorophosphate), PyBOP (benzotriazole-1-yl-oxy-tris-pyrrolidino-phosphonium hexafluorophosphate, EEDQ (2-ethoxy-1-ethoxycarbonyl-1,2-dihydro-quinoline), DCC (dicyclohexylcarbodiimide); DIPCDI (diisopropylcarbodiimide), MSNT (1-(mesitylene-2-sulfonyl)-3-nitro-1H-1,2,4-triazole, and arylsulfonyl halides, e.g. triisopropylbenzenesulfonyl chloride.

In some embodiments, the linker comprises an atom such as oxygen or sulphur, a unit such as —NH—, —$CH_2$—, —C(O)—, —C(O)NH—, or a hydrocarbyl group. The term "hydrocarbyl group" refers to an optionally substituted, linear or cyclic, straight or branched carbon chain that may be fully saturated or have one or more units of unsaturation. In certain embodiments, the hydrocarbyl group comprises one or more units of unsaturation. In some embodiments, the linker comprises a saturated or unsaturated $C_{1-30}$ hydrocarbyl group which is optionally substituted. In some embodiments, the linker comprises a saturated or unsaturated $C_{1-25}$ hydrocarbyl group which is optionally substituted. In some embodiments, the linker comprises a saturated or unsaturated $C_{1-20}$ hydrocarbyl group which is optionally substituted. In some embodiments, the linker comprises a saturated or unsaturated $C_{1-15}$ hydrocarbyl group which is optionally substituted. In some embodiments, the linker comprises a saturated or unsaturated $C_{1-10}$ hydrocarbyl group which is optionally substituted. In some embodiments, the linker comprises a saturated or unsaturated $C_{1-8}$ hydrocarbyl group which is optionally substituted. In some embodiments, the linker comprises a saturated or unsaturated $C_{1-6}$ hydrocarbyl group which is optionally substituted. In some embodiments, the linker comprises a saturated or unsaturated $C_{1-4}$ hydrocarbyl group which is optionally substituted. In some embodiments, the linker comprises a saturated or unsaturated $C_{1-2}$ hydrocarbyl group which is optionally substituted. In some embodiments of any of the foregoing, one or more saturated carbons of the chain are optionally replaced by —C(O)—, —C(O)C(O)—, —CONH—, —CONHNH—, —$CO_2$—, —OC(O)—, —$NHCO_2$—, —O—, —NHCONH—, —OC(O)NH—, —NHNH—, —NHCO—, —S—, —SO—, —$SO_2$—, —NH—, —$SO_2$NH—, or —$NHSO_2$—. In certain embodiments of the foregoing, the linker is rigid.

In some embodiments, any of the targeting moieties disclosed herein (e.g., any of the dyes disclosed herein) is covalently linked to any of the peptides disclosed herein by means of a linker comprising the structure of Compound II.

(Compound II)

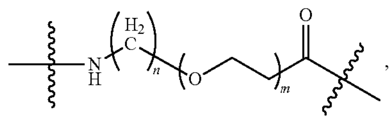

wherein n is 1-30, and wherein m is 0, 1, 2, 3, 4, or 5. In some embodiments, n is 1-25, 1-20, 1-15, 1-10, 1-8, 1-6, 1-4, 1-2 or 1. In some embodiments, n is 2. In some embodiments, m is 0.

In some embodiments, the linker is a β-Ala linker, a short polyethylene glycol (PEG) linker, or a long PEG linker. In particular embodiments, the linker is a β-alanine linker. In some embodiments, the PEG linker comprises 1, 2, 3, 4, 5, 6, 7, 8, 9, 10, 11, 12, 13, 14, 15, 16, 17, 18, 19, 20, 21, 22, 23, 24 or 25 units of PEG. In particular embodiments, the linker is β-alanine; 9-amino-4,7-dioxanonanoic acid or 6-amino-4-oxaohexanoic acid. In some embodiments, the linker is an FMOC derivatized linker.

In some embodiments, the conjugate comprises the structure of Compound III:

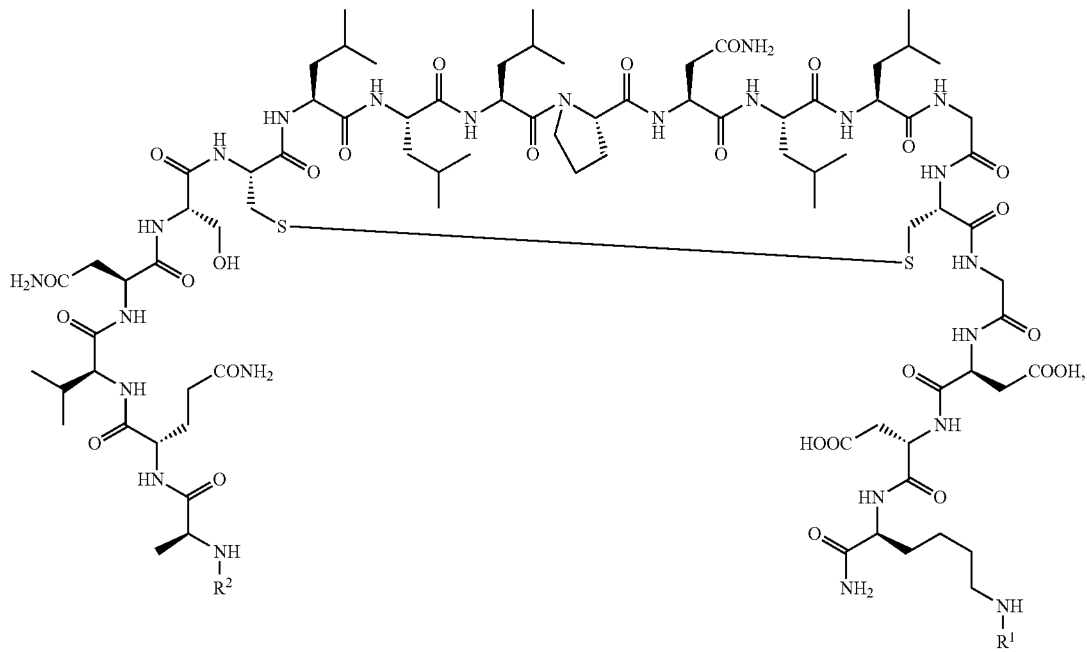

wherein R1 is biotin or hydrogen;
wherein $R^2$ comprises:

a)

Compound IV

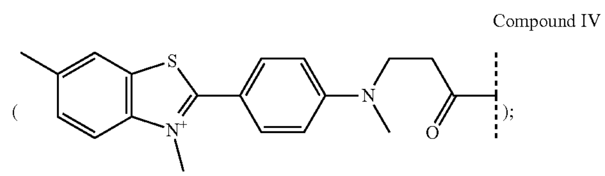

b)

Compound V

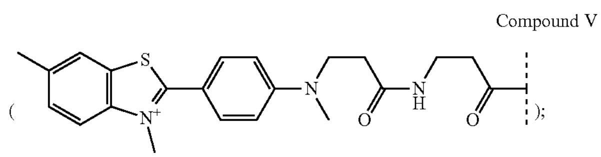

c)

Compound VI

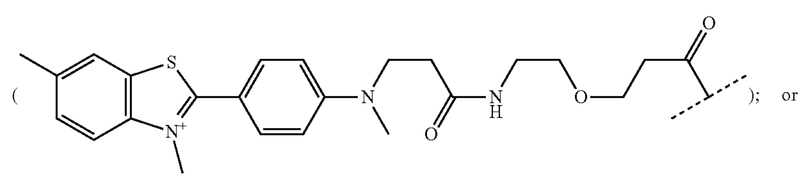

or

-continued d)

Compound VII

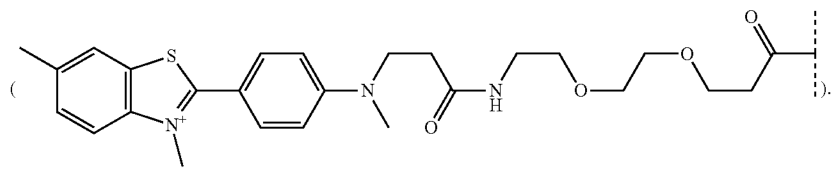

In some embodiments, $R^1$ is biotin. In some embodiments, $R^1$ is hydrogen. In particular embodiments, $R^2$ comprises Compound V Peptides can be conjugated to a targeting moiety (e.g., dye) at sites including an amino acid side-chain, the amino terminus, and the carboxy terminus. Peptides can be functionalized to bear reactive amino, thiol, sulfide, disulfide, hydroxyl, and carboxyl groups at any of these sites.

Any of the conjugates disclosed herein can be prepared by methods known to the person skilled in the art. Peptides comprised of amino acids and amino acid analogs may be covalently fused to a targeting moiety by conjugation with any of the dyes disclosed herein. In some embodiments, the dye bears an electrophilic linking moiety which reacts with a nucleophilic group on the peptide, e.g. amino terminus, or side-chain nucleophile of an amino acid. Alternatively, the dye may be in nucleophilic form, e.g. amino- or thiol-linking moiety, which reacts with an electrophilic group on the peptide, e.g. NHS of the carboxyl terminus or carboxyl side-chain of an amino acid. In some embodiments, the dye may be on a solid support, i.e. synthesis resin, during the conjugate reaction. Alternatively, the peptide may have been cleaved prior to conjugate to the dye. In certain embodiments, certain amino acid side-chains may allow conjugation with activated forms of any of the dyes disclosed herein. Aspartic acid, glutamic acid, lysine, arginine, cysteine, histidine, and tyrosine have reactive functionality for conjugations. By appropriate selection of protecting groups, certain reactive functionality on the peptide can be selectively unmasked for reaction with a targeting moiety (e.g., dye).

In some embodiments, peptides can be coupled to enzymes or to fluorescent labels directly or by the intermediary of a spacer group or of a linking group, such as a polyaldehyde, like glutaraldehyde, ethylenediaminetetraacetic acid (EDTA), diethylene-triaminepentaacetic acid (DPTA), or in the presence of coupling agents. Conjugates containing labels of fluorescein type can be prepared by reaction with an isothiocyanate.

In some embodiments, the methods known to the person skilled in the art existing for coupling the radioisotopes to the peptides either directly or via a chelating agent, such as EDTA, DTPA mentioned above can be used for the radioelements which can be used in diagnosis. It is likewise possible to perform labelling with sodium$^{125}$ by the chloramine T method [i] or else with technetium$^{99m}$ by the technique of Crockford et al., or attached via DTPA as described by Hnatowich.

In some embodiments, any of the conjugates of the disclosure bind to, for example, an Fc receptor (e.g., FcγRI). Such binding may take place in vivo, e.g. following administration of a conjugate, or it may take place in vitro, for example in ELISA, Western blotting, immunocytochemistry, immunoprecipitation, affinity chromatography, and biochemical or cell-based assays. Those skilled in the art are able to choose a suitable mode of determining binding of the peptide to the Fc receptor (e.g., FcγRI) according to their preference and general knowledge, in light of the methods disclosed herein. Such methods may include inter alia competitive ELISA and alpha screen.

In some embodiments, the disclosure provides for a dimer or oligomer of any of the conjugates disclosed herein. In some embodiments, the conjugates in the dimer or oligomer are linked to each other by means of a linker. In some embodiments, the peptide in the conjugate binds to two hFcγRIs. In some embodiments, the peptide in the conjugate activates Fc effector function. In some embodiments, the conjugate comprises two Fc mimetic peptides linked by a KKKKK linker (SEQ ID NO: 22).

In some embodiments, any of the conjugates disclosed herein is capable of recruiting an immune cell to the molecular aggregates. In some embodiments, the immune cell is a monocyte-derived cell. In some embodiments, the immune cell is a macrophage. In some embodiments, the immune cell is a monocyte. In some embodiments, the immune cell is a glial cell (e.g., a microglial cell). In some embodiments, the conjugate binds to the immune cell and facilitates activation of the immune cell. In some embodiments, the conjugate facilitates phagocytosis of at least a portion of the molecular aggregates.

4. Methods of Treatment

For any of the methods described herein, the disclosure contemplates the use of any of the conjugates and/or compositions described throughout the application. In addition, for any of the methods described herein, the disclosure contemplates the combination of any step or steps of one method with any step or steps from another method.

The terms "treatment", "treating", and the like are used herein to generally mean obtaining a desired pharmacologic and/or physiologic effect. "Treating" a condition or disease refers to curing as well as ameliorating at least one symptom of the condition or disease, and includes administration of a composition which reduces the frequency of, or delays the onset of, symptoms of a medical condition in a subject in need relative to a subject which does not receive the composition. "Treatment" as used herein covers any treatment of a disease or condition of a mammal, particularly a human, and includes: (a) preventing symptoms of the disease or condition from occurring in a subject which may be predisposed to the disease or condition but has not yet begun experiencing symptoms; (b) inhibiting the disease or condition (e.g., arresting its development); or (c) relieving the disease or condition (e.g., causing regression of the disease or condition, providing improvement in one or more symptoms). For example, treating an amyloidosis disease such as Alzheimer's Disease encompasses prevention of significant memory loss or cognitive decline, reduction in amyloid plaques, improvement in memory, and/or improvement or reduction of cognitive decline. Treatment of other amyloidosis conditions might encompass prevention/alleviation/reversal of diarrhea, weight loss, fatigue, glossomegaly, haemorrhage, somatic sensory deficits, postural hypotension, peripheral edema and splenomegaly. Treatment of atherosclerosis or heart disease might encompass clearance of cholesterol/lipid aggregates and/or prevention/alleviation/reversal of atherosclerosis and/or heart disease. Treatment of glycogen storage diseases might encompass clearance of glycogen deposits and/or any associated symptoms associated with that disease (locomotor defects, cognitive defects, hepatic defects, etc.).

In some embodiments, the disclosure provides for a method of recruiting an immune cell to an aggregate by contacting the aggregate with any of the conjugates disclosed herein. In some embodiments, the immune cell is any of the immune cells disclosed herein. In some embodiments, the immune cell is activated such that it is capable of clearing the aggregate (e.g., by phagocytosis or by recruiting/activating additional immune cells). In some embodiments, the aggregate is any of the aggregates disclosed herein. In some embodiments, the aggregate and immune cell are in vitro. In some embodiments, the aggregate and immune cell are in vivo. In some embodiments, the aggregate and immune cell are in an animal. In some embodiments, the animal is a mammal. In some embodiments, the mammal is a human. In some embodiments, the immune cell is a monocyte-derived cell. In some embodiments, the immune cell is a macrophage. In some embodiments, the immune cell is a monocyte. In some embodiments, the immune cell is a microglial cell.

In some embodiments, the disclosure provides for a method of treating a subject in need thereof with any one or more of the conjugates disclosed herein, wherein the subject has a disease or disorder associated with protein aggregates. In some embodiments, the protein aggregates comprise any one or more of alpha-synuclein, tau, amyloid beta, TDP-43, SOD1, FUS, TDP-43, prion protein, immunoglobulin light chain, transthyretin, fibrinogen, collagen, islet amyloid polypeptide, lysozyme, calcitonin, serum amyloid A protein, LECT2, amylin, gelsolin, fibrinogen A, prolactin, keratoepithelin, and $\beta_2$-microglobin, or aggregate-forming fragments or derivatives thereof. In some embodiments, the amyloid is composed of repetitive peptide sequences resulting from RAN-translation of nucleotide repeat expansions as seen in C9ORF72, Huntington's Disease, Fragile XA, Fragile XE, Friedrich's ataxia, Myotonic Dystrophy type 1 (DM1), Creutzfeldt-Jakob Disease, Myotonic Dystrophy type 2 (DM2), and Spinocerebellar ataxia types 8, 10, and 12 (SCAB, SCA10, SCA 12).

In some embodiments, the disease or disorder is an amyloidosis. In some embodiments, the amyloidosis is selected from the group consisting of: AL amyloidosis, AA amyloidosis, Alzheimer Disease, LECT2 amyloidosis, leptomeningeal amyloidosis, senile systemic amyloidosis, familial amyloid polyneuropathy, haemodialysis-associated amyloidosis, type 2 diabetes, Creutzfeldt-Jakob disease, Gerstmann-Straussler-Scheinker syndrome, Finnish type amyloidosis, cerebral amyloid angiopathy, familial visceral amyloidosis, primary cutaneous amyloidosis prolactinoma, familial corneal amyloidosis, Parkinson's Disease, amyotrophic lateral sclerosis, cerebral amyloid angiopathy, frontotemporal lobar dementia, medullary thyroid carcinoma, and B2M amyloidosis. In some embodiments, the amyloidosis is a familial amyloidosis. In some embodiments, the amyloidosis is systemic amyloidosis.

In some embodiments, the disclosure provides for a method of treating a subject in need thereof with any one or more of the conjugates disclosed herein, wherein the subject has a disease or disorder associated with polysaccharide aggregates. In some embodiments, the polysaccharide is glycogen. In some embodiments, the disease or disorder is a glycogen storage disease or disorder. In some embodiments, the disease or disorder is selected from the group consisting of Pompe Disease, von Gierke Disease, Forbes-Cori Disease, Andersen Disease, McArdle Disease, Hers Disease, Tarui's Disease, Fanconi-Bickel Syndrome, GSD IX, GSD X, GSD XI, GSD XII, GSD XIII, GSD XV, and Lafora Disease.

In some embodiments, the disclosure provides for a method of treating a subject in need thereof with any one or more of the conjugates disclosed herein, wherein the subject has a disease or disorder associated with lipid aggregates. In some embodiments, the lipid is cholesterol. In some embodiments, the lipid is sphingomyelin. In some embodiments, the lipid is globotriaosylceramide (Gb3) or glucocerebroside. In some embodiments, the disease or disorder is heart disease or atherosclerosis. In some embodiments, the disease or disorder is hypercholesterolemia. In some embodiments, the disease or disorder is Alzheimer's Disease or Parkinson's disease. In some embodiments, the disease or disorder is Fabry disease or Niemann-Pick Type A, Type B or Type C disease.

In some embodiments, the disclosure provides for a method of treating a subject in need thereof with any one or more of the conjugates disclosed herein, wherein the subject has a disease or disorder associated with nucleotide aggregates. In some embodiments, the disease or disorder is associated with RNA aggregates. In some embodiments, the disease or disorder is associated with DNA aggregates. In some embodiments, the disease or disorder is associated with aberrant microsatelite expansions. Conditions associated with aberrant microsatellite expansion (also referred to herein as microsatellite expansion diseases) include a number of neurological and neuromuscular diseases (O'Donnell, et al., 2002, Annu. Rev. Neurosci. 25: 315). These diseases or conditions are caused by microsatellite repeat expansions in coding and non-coding regions. These microsatellite repeat expansions may include, for example, CAG or CUG repeats, or variations thereof (e.g. CCUG). For example, the characterized coding region expansion diseases include Dentatorubral pallidoluysian atrophy (DRPLA), Huntington chorea (HD), Oculopharyngeal muscular dystrophy (OPMD), Spinobulbar muscular atrophy (SBMA), specific forms of Creutzfeldt-Jakob Disease and Spinocerebellar ataxia types 1, 2, 3, 6, 7, and 17 (SCA1, SCA2, SCA3, SCA6, SCAT, SCA1 7). The characterized non-coding region expansion diseases include Fragile XA, Fragile XE, Friedrich's ataxia, Myotonic Dystrophy type 1 (DM1), Myotonic Dystrophy type 2 (DM2), and Spinocerebellar ataxia types 8, 10, and 12 (SCAB, SCA10, SCA 12). Huntington's disease and Huntington's disease-like type 2 (HDL2) are also caused by a microsatellite expansion. Amyotrophic lateral sclerosis or fronotemporal dementia (FTD) are associated with repeat expansions in the chromosome 9 open reading frame 72 (C9ORF72) gene.

In some embodiments, any of the conjugates described herein may be combined with an alternative therapy. It will be appreciated that treatment of protein aggregation associated diseases according to the present invention may be combined with other treatment methods known in the art (i.e., combination therapy). Thus, in the cases for amyloidosis, compounds of the present invention may be co-administered (simultaneously or separately) with additional drugs such as anti-amyloid drugs. Examples of such anti-amyloid drugs include, but are not limited to, amyloid destabilizing antibodies, amyloid destabilizing peptides and anti-amyloid small molecules. Other combination therapies may include a therapeutically effective amount of at least one drug selected from the group consisting of BACE inhibitors; muscarinic antagonists; cholinesterase inhibitors; gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; GABAA inverse agonists; inhibitors of amyloid aggregation; glycogen synthase kinase beta inhibitors; promoters of alpha secretase activity; PDE-10 inhibitors; Exelon (rivastigmine); Cognex (tacrine); Tau kinase; anti-Abeta vaccine; APP ligands; agents that upregulate insulin cholesterol lowering agents; cholesterol absorption inhibitors; fibrates; LXR agonists; LRP mimics; nicotinic receptor agonists; H3 receptor antagonists; histone deacetylase inhibitors; hsp90 inhibitors; ml muscarinic receptor agonists; 5-HT6 receptor antagonists; mGluR1; mGluR5; positive allosteric modulators or agonists; mGluR2/3 antagonists; anti-inflammatory agents that can reduce neuroinflammation; Prostaglandin EP2 receptor antagonists; PAI-1 inhibitors; and agents that can induce Abeta efflux.

Other combination therapies may include a therapeutically effective amount of at least one therapy selected from the group consisting of physical therapy, massage, cannabinoids (See, e.g., Ramirez, et al, The Journal of Neuroscience, Feb. 23, 2005, 25(8):1904-1913); dimebon (See, e.g., R S Doody, et al., The Lancet 372:207-215 (2008); Selective estrogen receptor molecules (SERMs), e.g., raloxifene (EVISTA®); antihypertensives, including alpha-blockers, beta-blockers, alpha-beta blockers, angiotensin-converting enzyme inhibitors, angiotensin receptor blockers (ARBs, such as valsartan (e.g., DIOVAN®)), calcium channel blockers, and diuretics (See, e.g., I Hajjar, et al, The Journals of Gerontology Series A: Biological Sciences and Medical Sciences 60:67-73 (2005)); and antioxidants such as garlic extract, curcumin, melatonin, resveratrol, Ginkgo biloba extract, green tea, vitamin C and vitamin E (See, e.g., B Frank, et al., Ann Clin Psychiatry 17(4):269-86 (2005)).

In cases of cholesterol related diseases or disorders, any of the conjugates described herein may be combined with cholesterol-lowering and/or heart protective drugs such as statins, e.g., atorvastatin (LIPITOR®), cerivastatin (BAYCOL®), fluvastatin (e.g., LESCOL®), mevastatin, pitavastatin (e.g., LIVALO®), pravastatin (e.g., PRAVACHOL®), rosuvastatin (e.g., CRESTOR®) and simvastatin (e.g., ZOCOR®).

5. Pharmaceutical Compositions

In some embodiments, any of the conjugates described herein may be formulated into pharmaceutical compositions. Pharmaceutical compositions for use in accordance with the present disclosure may be formulated in conventional manner using one or more physiologically acceptable carriers or excipients. Such formulations will generally be substantially pyrogen-free, in compliance with most regulatory requirements.

In certain embodiments, the therapeutic method of the disclosure includes administering the composition systemically, or locally as an implant or device. When administered, the therapeutic composition for use in this disclosure is in a pyrogen-free, physiologically acceptable form. Therapeutically useful agents other than the conjugates which may also optionally be included in the composition as described above, may be administered simultaneously or sequentially with the subject compounds in the methods disclosed herein.

In some embodiments, conjugates disclosed herein will be administered parentally, and particularly intravenously or subcutaneously. In some embodiments, the conjugates are administered intrathecally. In some embodiments, the conjugates are administered intramuscularly. In some embodiments, the conjugates are administered intracerebroventrically. In some embodiments, the conjugates are administered intranasally. Pharmaceutical compositions suitable for parenteral administration may comprise one or more conjugates in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The compositions and formulations may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration Further, the composition may be encapsulated or injected in a form for delivery to a target tissue site. In certain embodiments, compositions of the present invention may include a matrix capable of delivering one or more conjugates to a target tissue site, providing a structure for the developing tissue and optimally capable of being resorbed into the body. For example, the matrix may provide slow release of the conjugates. Such matrices may be formed of materials presently in use for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalcium phosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalcium phosphate. The bioceramics may be altered in composition, such as in calcium-aluminate-phosphate and processing to alter pore size, particle size, particle shape, and biodegradability.

In certain embodiments, methods of the invention can be administered orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. An agent may also be administered as a bolus, electuary or paste.

In solid dosage forms for oral administration (capsules, tablets, pills, dragees, powders, granules, and the like), one or more therapeutic compounds of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

The compositions of the invention may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

It is understood that the dosage regimen will be determined by the attending physician considering various factors which modify the action of the subject conjugates of the invention. The various factors include, but are not limited to, the patient's age, sex, and diet, the severity disease, time of administration, and other clinical factors. Optionally, the dosage may vary with the type of matrix used in the reconstitution and the types of compounds in the composition. The addition of other known growth factors to the final composition, may also affect the dosage. Progress can be monitored by periodic assessment of bone growth and/or repair, for example, X-rays (including DEXA), histomorphometric determinations, and tetracycline labeling.

Another targeted delivery system for conjugates is a colloidal dispersion system. Colloidal dispersion systems include macromolecule complexes, nanocapsules, microspheres, beads, and lipid-based systems including oil-in-water emulsions, micelles, mixed micelles, and liposomes. In some embodiments, the colloidal system of this invention is a liposome. Liposomes are artificial membrane vesicles which are useful as delivery vehicles in vitro and in vivo. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

The disclosure provides formulations that may be varied to include acids and bases to adjust the pH; and buffering agents to keep the pH within a narrow range.

EXEMPLIFICATION

The invention now being generally described, it will be more readily understood by reference to the following examples, which are included merely for purposes of illustration of certain embodiments of the present invention, and are not intended to limit the invention.

Example 1: Generation of BDB

Compound 1 is a carboxylic acid derivative of thioflavin T. This is added as the terminal residue to the biotinylated synthetic cyclic peptide shown in FIG. 1, which is a derivative of the cp33 peptide (Bonetto S et al. FASEB J. 2009; 23(2):575-85). The resulting conjugate is referred to as "BDB" in the Examples provided below.

Example 2: Determining the Binding of BDB to Amyloids

Figure 2:
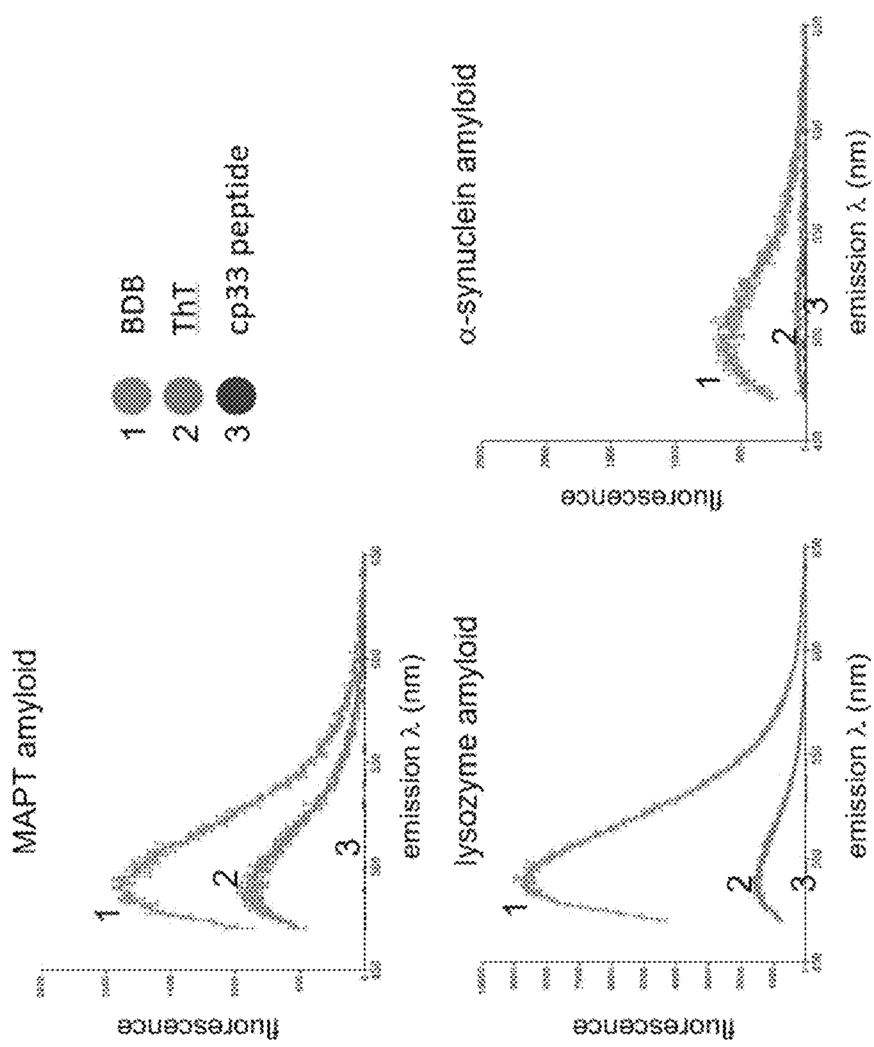
FIG. 2 shows data demonstrating BDB binding to various amyloids. As shown, BDB and Tht have increased fluorescence in the presence of amyloid proteins, as compared to amyloid-free control reactions. The cp33 peptide not conjugated with Compound 1 did not show a fluorescence signal in the presence of amyloid, as compared to amyloid-free control reactions.

The binding of BDB to various amyloid proteins was evaluated in vitro using a fluorometric assay. Results are summarized in FIG. 2.

The amyloid proteins (hen lysozyme (hLys), human full-length alpha synuclein, and human tau P301S) were individually prepared for use in the fluorometric assay. hLys (Sigma) was dissolved in 136.8 mM NaCl, 2.68 mM KCl, 0.01% w/v $NaN_3$, pH 2 at a concentration of 1.45 mg/ml and incubated at 55° C. for 24 h in an orbital shaker at 150 rpm. Human full length alpha synuclein (Alexotech) was dissolved in 150 mM NaCl, 1% v/v triton-x100 in PBS at a concentration of 2.2 mg/ml and incubated at 37° C. for 72 h in an orbital shaker at 250 rpm. Human tau P301S was incubated at 8 mg/ml with 4 mg/ml heparin (Sigma) in PBS, 30 mM 3-(N-morpholino) propanesulfonic acid (MOPS) (pH 7.2) at 37° C. for 72 h. The solution was mixed with nine volumes of PBS with 1% v/v sarkosyl (Sigma) and left rocking for 1 h at room temperature. Insoluble tau was pelleted by ultracentrifugation for 1 h at 4° C. and the pellet resuspended in PBS and sonicated at 100 W for 3×20 s (Hielscher UP200St ultrasonicator).

The binding of the BDB to amyloid was detected using a fluorometric assay. The amyloid binding was detected with the use of one of three fluorescent reporters solutions (30 μM BDB, cp33 peptide (Bonetto S et al. FASEB J. 2009; 23(2):575-85) or Thioflavin T (ThT) (Sigma) solution, in PBS). One microlitre of amyloid suspension (30 μM tau or lysozyme or 150 μM α-synuclein) was mixed with 19 μl of one of three reporter solutions in black 384 well polystyrene plates (Greiner Bio-one). An Envision plate reader was set to excite at 450 nm and measure emission within the range 460-680 nm. The corresponding fluorescence signals of the reporter solutions were subtracted from the experimental data. As demonstrated in FIG. 2, BDB and Tht have increased fluorescence in the presence of amyloid proteins. The cp33 peptide, not conjugated with Compound 1, did not show a fluorescence signal in the presence of amyloid.

Example 3: Determining the Binding of BDB to Activated Phagocytic Cells

In order to determine the binding affinity of BDB to activated phagocytic cells, activated and non-activated U937 cells or murine primary macrophages were resuspended in the presence of BDB, biotinylated human IgG1, or PBS. The cells were then stained using either AF488-streptavidin conjugate, APC-Cy7 dead/live stain, or dead/live stain only and measured using fluorescence activated cell sorting (FACS).

Figure 3:
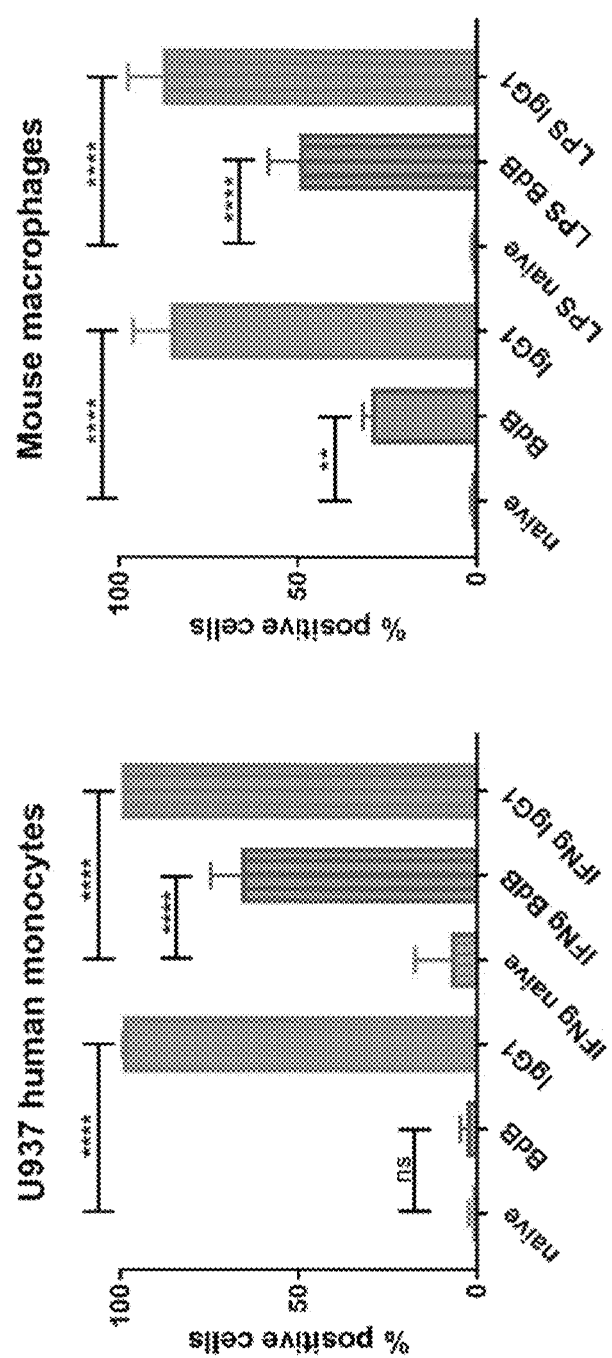
FIG. 3 shows data for BDB binding to activated phagocytic cells from humans and mice. As shown, U937 cells treated with IFNγ (IFNg) or murine primary macrophages treated with LPS, showed enhanced binding of BDB in flow-cytometry experiments. These results are consistent with BDB binding to the increased surface expression of Fc receptors. IgG1 binds multiple receptors with high affinity and labels cells irrespective of activation status.

Specifically, U937 cells were cultured in RPMI 1640+2 mM Glutamine+10% v/v foetal bovine serum (FCS) for 48 h in the absence or presence of 100 μg/ml human IFNγ (Thermo Fisher Scientific). Murine primary macrophages were cultured for 48 h in the absence or presence of 100 μg/ml LPS (Sigma). Aliquots of $5\times10^5$ cells were centrifuged 3 min at 300 g and resuspended either in 50 μl of 10 μM BDB, 1 μM biotinylated human IgG1 or PBS. Samples were incubated at 4° C. for 1 h and then centrifuged for 3 min at 100 g. Cells were resuspended in 50 μl of either AF488-streptavidin conjugate (Thermo Fisher Scientific, 1:500 in PBS) with APC-Cy7 dead/live stain (Thermo Fisher Scientific, 1:2000 in PBS) or dead/live stain only. Samples were incubated at 4° C. for 30 min and then centrifuged for 3 min at 100 g. Samples were washed with 200 μl cold PBS and resuspended in 250 μl PBS for analysis using a FACS Canto II, with $10^4$ events recorded per condition. Using FlowJo software, cells were visualised using forward and side scatter plots (FSC vs. SSC) and live cells were gated according to their live/dead staining. The percentage of live cells positive for AF488 signal was identified for each condition and plotted. The experiment was repeated three times and results present as the mean (+/−SD). A one-way ANOVA was used estimate the significance of differences between the conditions ( P<0.01,  P<0.0001). As demonstrated in FIG. 3**, U937 cells treated with IFNγ (IFNg) or murine primary macrophages treated with LPS, showed enhanced binding of BDB. These results are consistent with BDB binding to the increased surface expression of Fc receptors. IgG1 binds multiple receptors with high affinity and labels cells irrespective of activation status.

Example 4: Titrating BDB and IgG1 Binding to IFNg Stimulated U937 Cells

The binding of BDB and IgG1 to IFNγ stimulated U937 cells was determined using the following methods. U937 cells were cultured in RPMI 1640+2 mM Glutamine+10% v/v FCS for 48 h in the presence of 100 μg/ml human IFNγ. Aliquots of $5\times10^5$ U937 cells were centrifuged 3 min at 300 g and resuspended in 50 μl of either BDB or biotinylated IgG1 at concentrations ranging from 0.01-5 μM or 0.01-1 μM respectively. The staining and FACS analysis were performed as described above.

Figure 4:
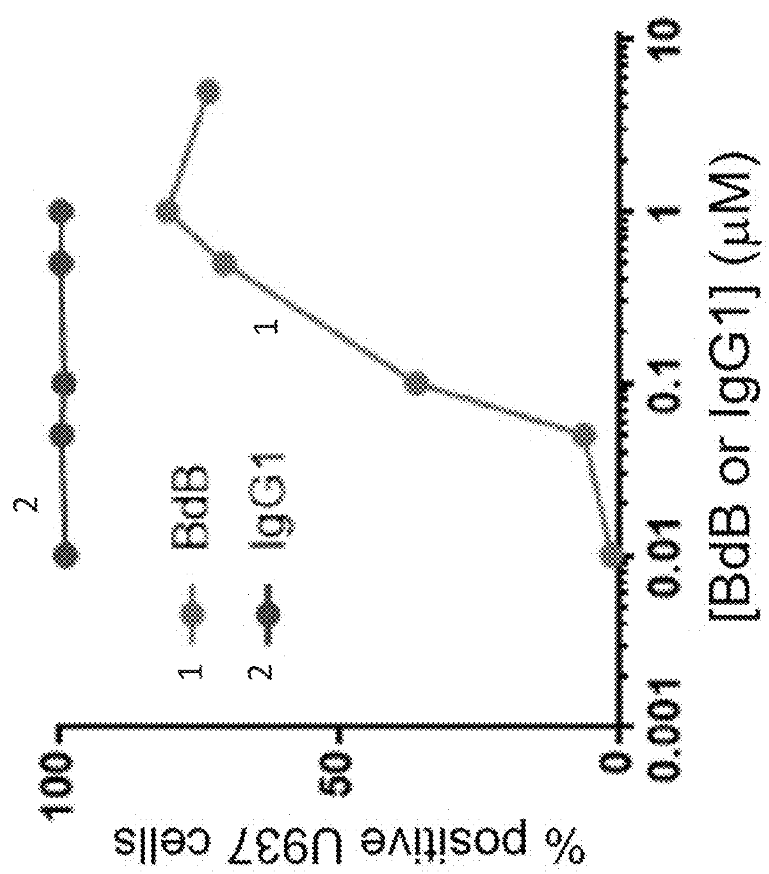
FIG. 4 shows the binding curve for BDB to IFNγ-activated U937 cells. As shown, increasing concentrations of BDB resulted in as many as 80% of IFNγ-activated U937 cells being bound, in flow-cytometry experiments. Half-maximal binding was see at approximately 200 nM BDB. IgG1 bound to all cells under the same conditions.

FIG. 4 demonstrates that as the concentration of BDB increased, as many as 80% of IFNg-activated U937 cells were bound. Half-maximal binding was see at approximately 200 nM BDB. IgG1 bound to all cells under the same conditions.

Example 5: Competing the Binding of BDB and Cp33 Peptide to Fc-Receptors Using Unlabelled Human IgG1

A competitive assay between human IgG1 and BDB or cp33 peptide was conducted in order to determine the specific binding of BDB and cp33 peptides to the Fc receptor. Specifically, U937 cells were cultured in RPMI 1640+2 mM Glutamine+10% v/v FCS for 48h in the presence of 100 μg/ml human IFNγ. Aliquots of $5\times10^5$ cells were centrifuged for 3 min at 300 g and resuspended in 50 μl of either 1 μM BDB or cp33 in the presence or absence of a control monoclonal human IgG1 (Nip228, MedImmune Ltd) at concentrations in the range 0.001-5 μM. The staining and FACS analysis were performed as described above.

Figure 5:
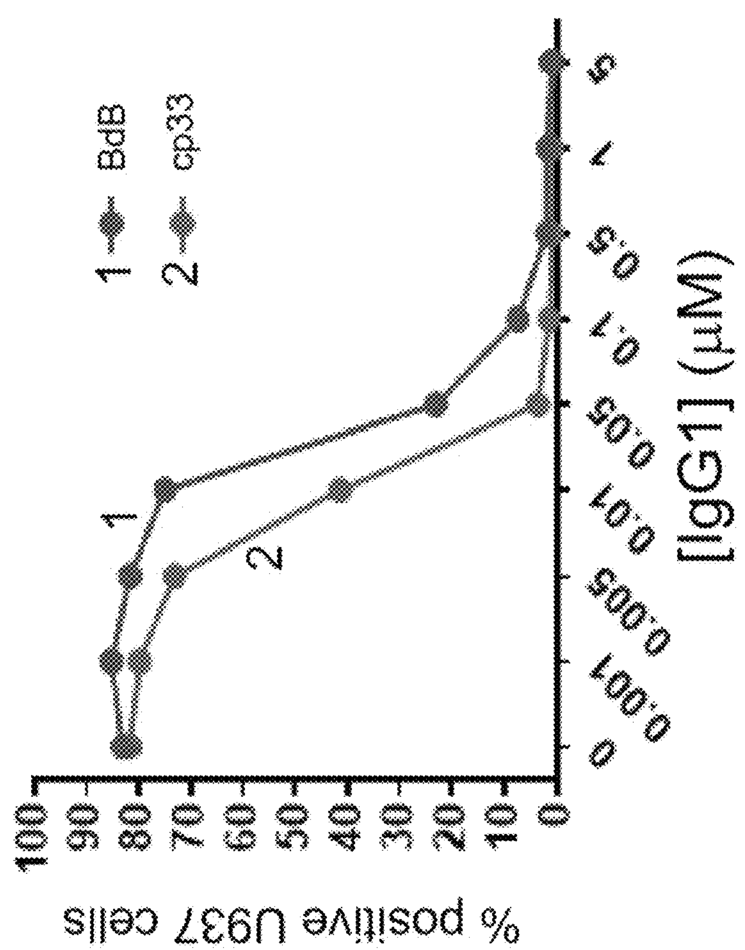
FIG. 5 shows data from a competition assay between human IgG1, BDB, and cp33 peptide for binding to IFNγ-activated U937 cells, in flow-cytometry experiments. As shown, when the concentration of human IgG1 increases above approximately 10 nM, both the BDB and cp33 peptide are displaced from binding to IFNγ-activated U937 cells. This competition is consistent with the BDB and cp33 peptides binding to the Fc receptor.

FIG. 5 demonstrates that as the concentration of human IgG1 increases above approximated 10 nM, both the BDB and cp33 peptide are displaced from binding to IFGγ-activated U937 cells. This competition is consistent with the BDB and cp33 peptides binding to the Fc receptor.

Example 6: Demonstrating the Colocalization of the BDB and Amyloid to the Surface of U937 Cells IFNγ-activated U937 cells, a human macrophage cell line, were incubated with either BDB, cp33 peptide, or vehicle in the presence or absence of Alexa Fluor™ 647-labelled hLys amyloid in order to determine if the IFNγ-activated U937 cells have increased binding of amyloid in the presence of BDB or cp33 peptide as compared to vehicle.

Specifically, hLys were labelled with the fluorescent dye alexa 647, using the Alexa Fluor™ 647 Microscale Protein Labelling Kit (Thermo Fisher Scientific) according to the manufacturer's instructions with the following modifications: after protein labelling, the solution was made up to 500 μl with PBS and the sample centrifuged at 20800 for 40 min. The supernatant was discarded and the pellet washed with PBS, resuspended in 500 μl PBS and the centrifugation repeated. The final pellet was resuspended in 100 μl of PBS.

U937 cells were cultured in RPMI 1640+2 mM Glutamine+10% v/v FCS for 48 h in the presence of 100 μg/ml human IFNγ. Aliquots of $5\times10^5$ cells were centrifuged 3 min at 300 g and resuspended in 50 μl of either 1 μM BDB or cp33 and then incubated with either 1 or 0.1 μM AF647-hLyz. The staining and FACS analysis were performed as before, this time reporting the percentage of live cells positive for both AF488-streptavidin and AF647 h-Lyz.

Figure 6:
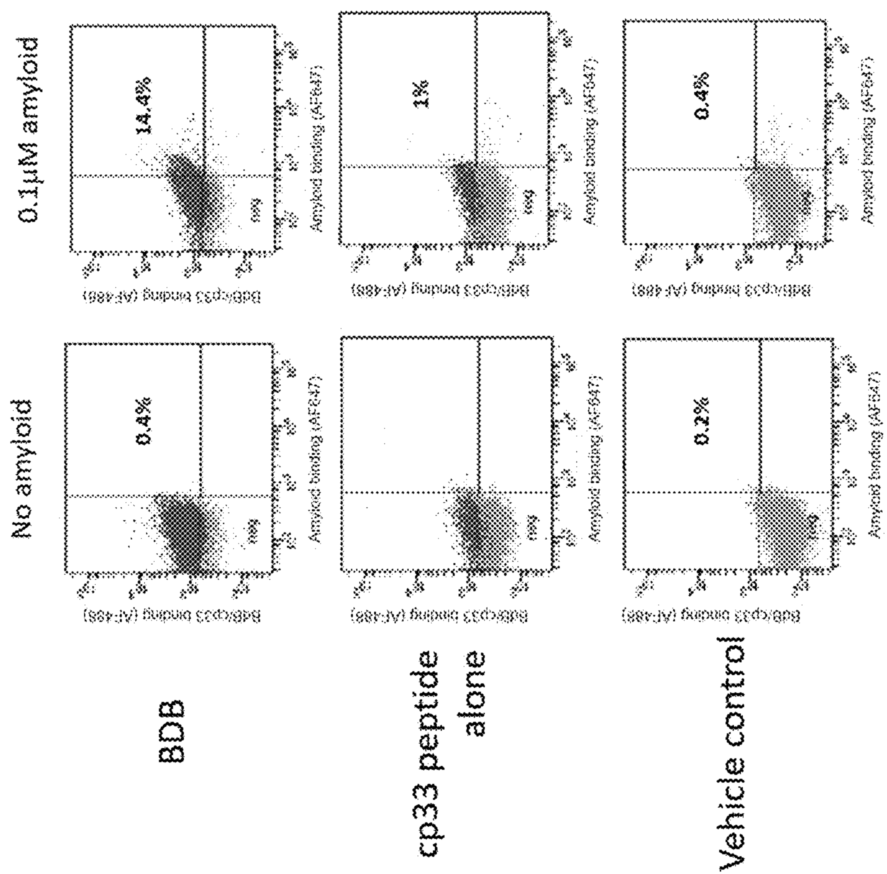
FIG. 6 shows data comparing the localization of amyloid to the surface of IFNγ-activated U937 cells treated with BDB, cp33 peptide, or vehicle control, in flow-cytometry experiments. As shown, BDB enhances the binding of amyloid to IFNγ-activated U937 cells. Both BDB and cp33 peptide show cell binding irrespective of whether amyloid is present (upward displacement of the cell population on the y-axis in top four panels). Up to 14.4% of IFNγ-activated U937 cells are observed binding amyloid in the presence of BDB as compared to 1.0% in the presence of cp33 peptide or 0.4% when treated with vehicle.

FIG. 6 compares the localization of amyloid to the surface of IFNγ-activated U937 cells treated with BDB, cp33 peptide, or vehicle control. Both BDB and cp33 peptide show cell binding irrespective of whether amyloid is present (displacement on y-axis in top four panels). Up to 14.4% of IFNγ-activated U937 cells are observed binding amyloid in the presence of BDB as compared to 1.0% in the presence of cp33 peptide or 0.4% when treated with vehicle. These results demonstrate that BDB enhances the binding of amyloid to IFGγ-activated U937 cells.

Example 7: Measuring Phagocytosis of Labelled Amyloid

Macrophage-differentiated U937 cells were co-incubated with pHrodo-red labelled amyloid, BDB, cp33 peptide, or control in order to determine the amount of amyloid phagocytosed under various conditions. hLys amyloid fibrils were generated as described above and were labelled with the pHrodo Red Microscale Labeling Kit (ThermoFisher) according to the manufacturers instruction except that unincorporated label was removed from the labelled amyloid by three rounds of centrifuging at 20,000×g in a microfuge, discarding the supernatant and resuspending the amyloid pellet in PBS. U937 cells were differentiated into macrophages in the presence of 100 μg/ml M-CSF (Peprotech), 1 μg/ml PMA (Sigma) and 100 μg/ml IFNγ (Thermo Fisher Scientific) for 4 days. $8\times10^5$ cells/condition were centrifuged for 3 min at 300 g and resuspended in 50 μl of 1 μM BDB, 1 μM cp33, 1 μM BDB with 0.1 μM labelled amyloid, 1 μM cp33 with 0.1 μM labelled amyloid, 0.1 μM labelled amyloid or a 1:100 PBS dilution of a pHrodo Red-labelled *E. coli* suspension (Thermo Fisher Scientific). The cells were incubated at 4° C. for 1 h, centrifuged for 3 min at 100 g and resuspended in 300 μl of RPMI media containing 100 μg/ml M-CSF, 1 μg/ml PMA and 100 μg/ml IFNg. For each condition, a 100 μl suspension of cells was plated to the wells of black 96-well plates with clear bottom (Greiner Bio-one).

The plates were placed in an IncuCyte instrument and settings programmed to scan both in phase contrast and the red fluorescence channel hourly for 48 h. Raw data for each time point was then processed using the IncuCyte Zoom software with a red channel processing algorithm. A metric of Total Red Object Area ($\mu m^2$/well) was used to quantify the appearance of pHrodo red fluorescence within cells.

Figure 7:
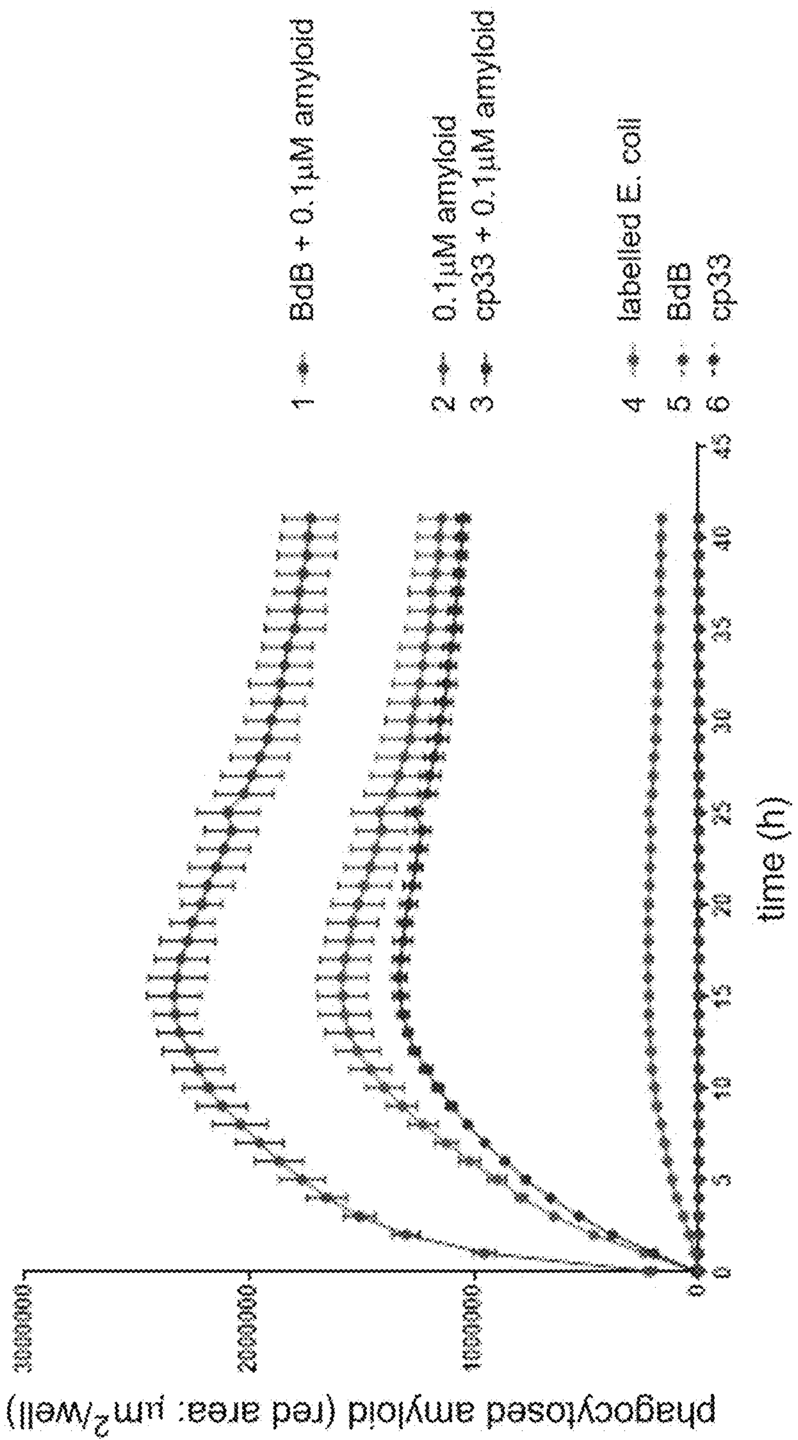
FIG. 7 shows labelled amyloid phagocytosis data for macrophage-differentiated U937 cells co-incubated with pHrodo-red labelled amyloid, BDB, cp33 peptide, or control. As shown, BDB enhances the phagocytosis of amyloid by macrophage-differentiated U937 cells. Red colour (y-axis) reported phagocytosed amyloid; this signal increased more rapidly and achieved a greater amplitude in cells treated with BDB-amyloid (1) as compared to cp33-amyloid (3) or amyloid alone (2). pHrodo-red *E. coli* were added as a positive control (4). In the absence of amyloid, BDB (5) and the cp33 peptide (6) did not generate a signal.

FIG. 7 demonstrates that BDB enhances the phagocytosis of amyloid by macrophage-differentiated U937 cells. Red colour (y-axis) reported phagocytosed amyloid; this signal increased more rapidly and achieved a greater amplitude in cells treated with BDB-amyloid (1) as compared to cp33-amyloid (3) or amyloid alone (2). pHrodo-red *E. coli* were added as a positive control (4). In the absence of amyloid, BDB (5) and the cp33 peptide (6) did not generate a signal.

In a separate experiment, several different BDB constructs were each tested in the same phagocytosis assay discussed above. In this experiment, the BDB constructs comprised the structure of Compound III:

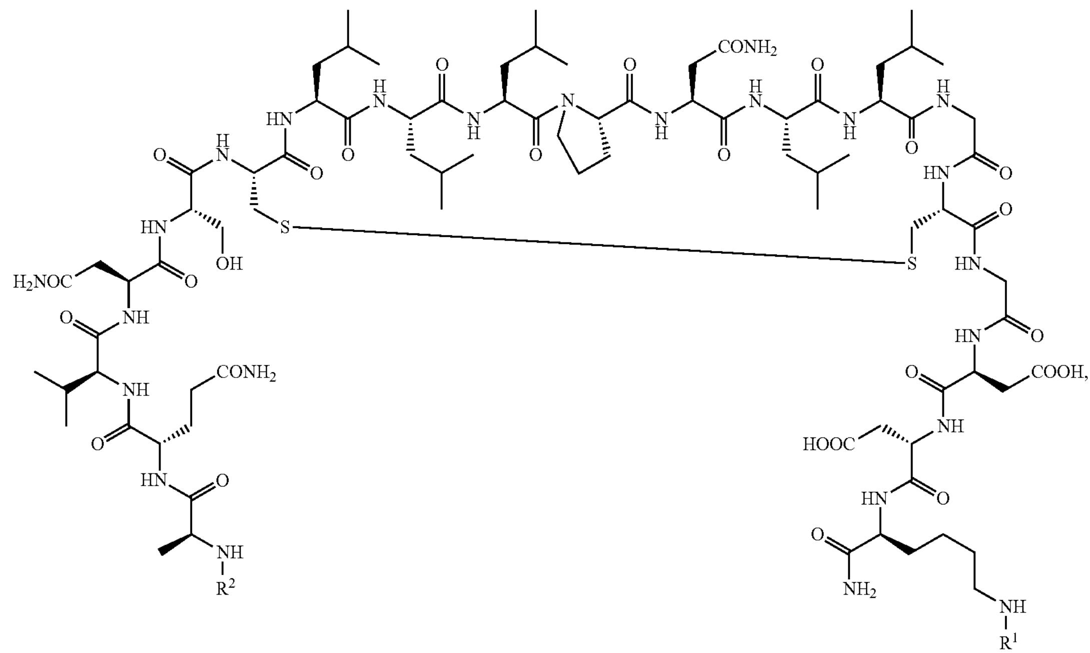

wherein $R^1$ was biotin (which may be optionally replaced with hydrogen); $R^2$ was:

a) the dye alone

Compound IV

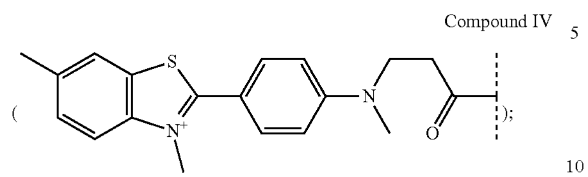

b) the dye with a beta-alanine linker

Compound V

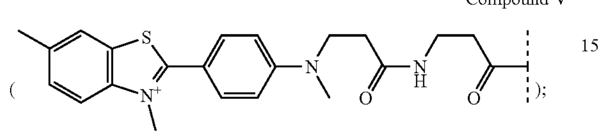

c) the dye with a 6-amino-4-oxahexanoate linker

Compound VI

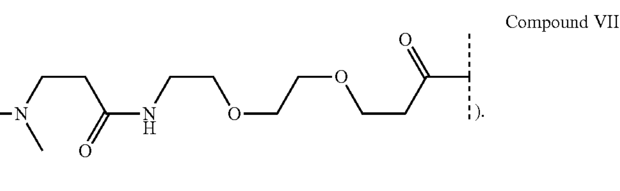

d) the dye with a 9-amino-4,7-dioxanonanoate linker

Compound VII

Figure 8:
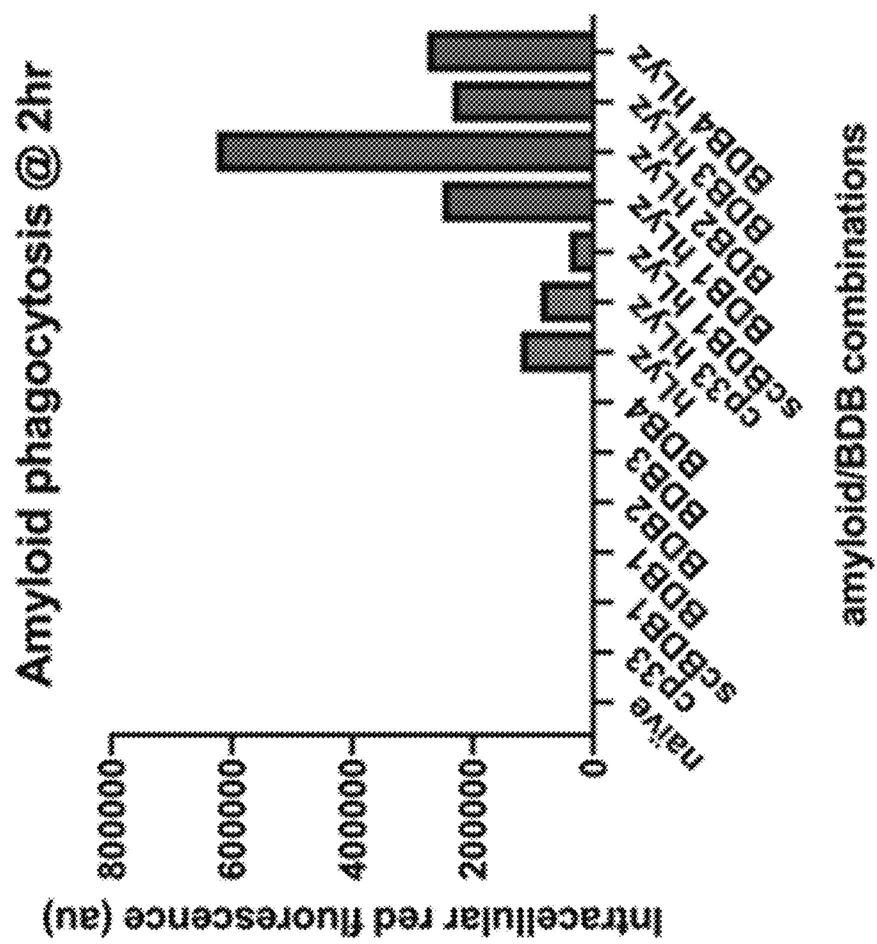
FIG. 8 shows labelled amyloid phagocytosis data for macrophage-differentiated U937 cells co-incubated with pHrodo-red labelled lysozyme amyloid, cp33 or various BDB constructs. Cp33=peptide alone (no dye); scBDB1=BDB1 with scrambled peptide portion; BDB1=linkerless BDB construct; BDB2=BDB construct comprising the beta-alanine linker; BDB3=BDB construct comprising the 6-amino-4-oxahexanoate linker; and BDB4=BDB construct comprising the 9-amino-4,7-dioxanonanoate linker. Phagocytosis was plotted in arbitrary fluorescence units at the 2 hour timepoint using the automated analysis of pHrodo-red pixels with an Incucyte microscope.

In this experiment, it was surprisingly found that the BDB with the more rigid beta-alanine linker induced a more than two-fold greater rate of amyloid phagocytosis as compared to the BDB lacking the linker or to the BDBs having the longer 6-amino-4-oxahexanoate or 9-amino-4,7-dioxanonanoate linkers (FIG. 8).

Figure 9:
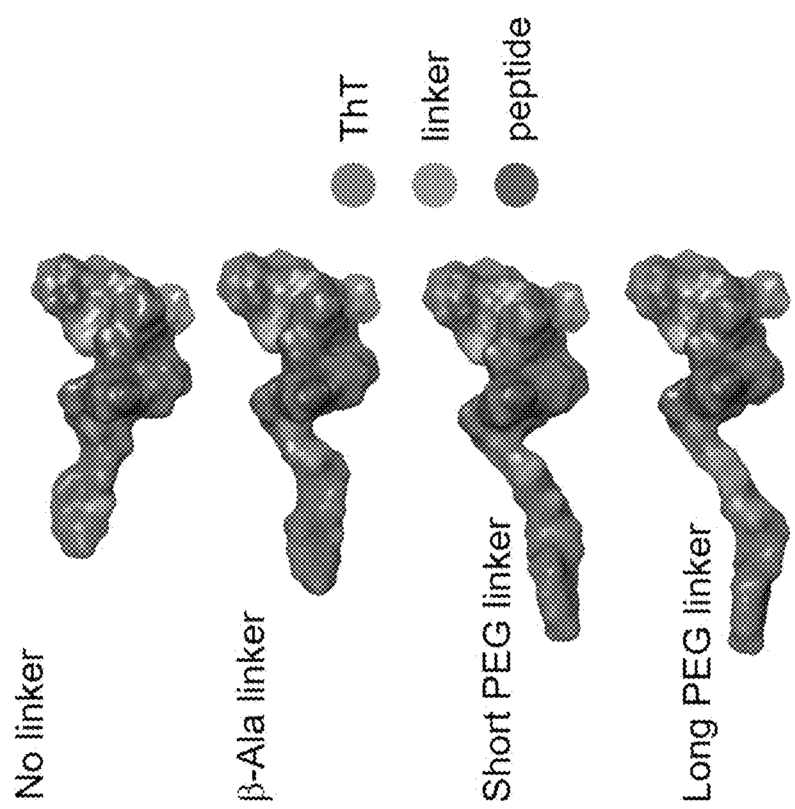
FIG. 9 shows space-filing models of how the amyloid-binding domain (pink) may be separated from the FcR-binding domain (grey) by linkers of differing length (green). The structural effects of adding linkers between the amyloid binding and FcR-binding moieties is demonstrated. In some embodiments, linkers may comprise β-alanine; 9-amino-4,7-dioxanonanoic acid (short PEG linker) and 6-amino-4-oxaohexanoic acid (long PEG linker).

Example 8: Structural Effects of Adding Linkers Between the Amyloid Binding and FcR-Binding Moieties Space-filling models were developed to determine the structural effects of adding linkers between the amyloid binding and FcR-binding moieties. Specifically, FIG. 9 demonstrates a comparison between models which use no linker, a β-Ala linker, a short PEG linker, and a long PEG linker (FMOC derivatized β-Alanine; 9-amino-4,7-dioxanonanoic acid; and 6-amino-4-oxaohexanoic acid).

We claim:

1. A conjugate comprising a peptide having the amino acid sequence of AQVNSCLLLPNLLGCGDDK (SEQ ID NO: 3) fused to a targeting moiety that targets molecular aggregates having the formula of Compound I:

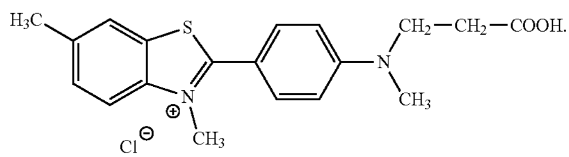

2. A method of treating an amyloidosis by administering any one or more of the conjugates of claim 1.

3. The method of claim 2, wherein the amyloidosis is selected from the group consisting of: AL amyloidosis, AA amyloidosis, Alzheimer Disease, LECT2 amyloidosis, leptomeningeal amyloidosis, senile systemic amyloidosis, familial amyloid polyneuropathy, haemodialysis-associated amyloidosis, type 2 diabetes, Creutzfeldt-Jakob disease, Gerstmann-Straussler-Scheinker syndrome, Finnish type amyloidosis, cerebral amyloid angiopathy, familial visceral amyloidosis, primary cutaneous amyloidosis prolactinoma, familial corneal amyloidosis, Parkinson's Disease, amyotrophic lateral sclerosis, cerebral amyloid angiopathy, frontotemporal lobar dementia, medullary thyroid carcinoma, and B2M amyloidosis.

4. The method of claim 2, wherein the amyloidosis is a familial amyloidosis.

5. The method of claim 4, wherein the amyloidosis is systemic amyloidosis.

6. A method of reducing levels of an aggregate in a cell or tissue by treating the cell or tissue with the conjugate of claim 1.

7. A conjugate comprising the structure of Compound III:

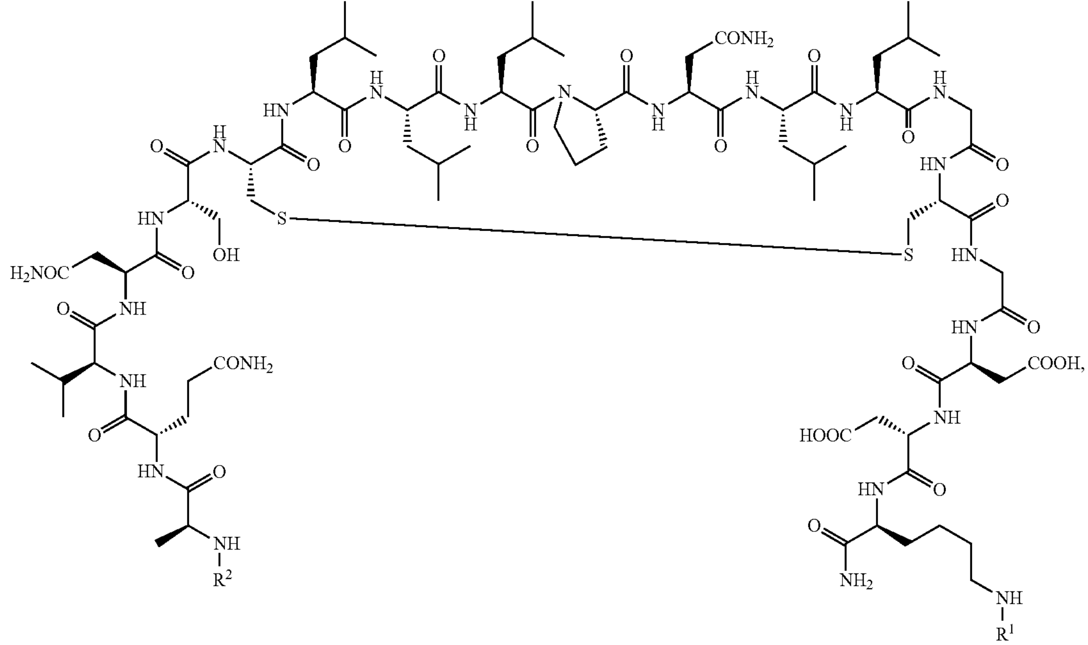

wherein $R^1$ is biotin or hydrogen;
wherein $R^2$ comprises:

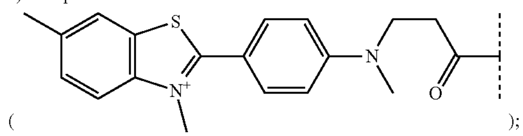

-continued b) Compound V

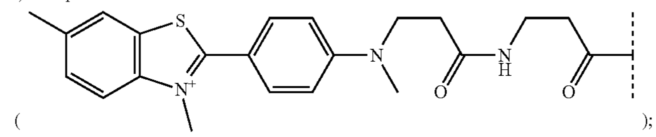

( );

c) Compound VI

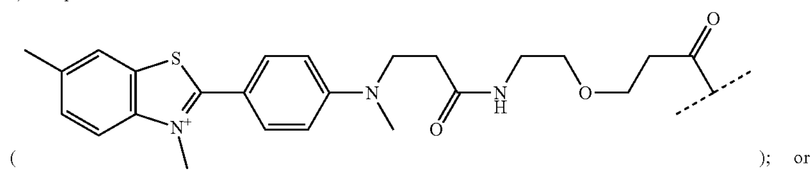

( ); or d) Compound VII

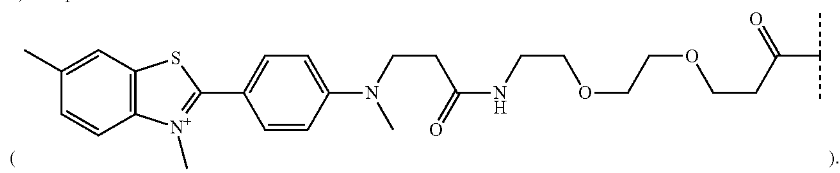

( ).

8. A method of treating an amyloidosis by administering any one or more of the conjugates of claim 7.

9. The method of claim 8, wherein the amyloidosis is selected from the group consisting of: AL amyloidosis, AA amyloidosis, Alzheimer Disease, LECT2 amyloidosis, leptomeningeal amyloidosis, senile systemic amyloidosis, familial amyloid polyneuropathy, haemodialysis-associated amyloidosis, type 2 diabetes, Creutzfeldt-Jakob disease, Gerstmann-Straussler-Scheinker syndrome, Finnish type amyloidosis, cerebral amyloid angiopathy, familial visceral amyloidosis, primary cutaneous amyloidosis prolactinoma, familial corneal amyloidosis, Parkinson's Disease, amyotrophic lateral sclerosis, cerebral amyloid angiopathy, frontotemporal lobar dementia, medullary thyroid carcinoma, and B2M amyloidosis.

10. The method of claim 8, wherein the amyloidosis is a familial amyloidosis.

11. The method of claim 10, wherein the amyloidosis is systemic amyloidosis.

12. A method of reducing levels of an aggregate in a cell or tissue by treating the cell or tissue with the conjugate of claim 7.

* * * * *